United States Patent
Riehl

(10) Patent No.: US 11,497,924 B2
(45) Date of Patent: Nov. 15, 2022

(54) SYSTEMS AND METHODS FOR ENABLING POINT OF CARE MAGNETIC STIMULATION THERAPY

(71) Applicant: Realize MedTech LLC, Naples, FL (US)

(72) Inventor: Mark E. Riehl, Naples, FL (US)

(73) Assignee: Realize MedTech LLC, Naples, FL (US)

(*) Notice: Subject to any disclaimer, the term of this patent is extended or adjusted under 35 U.S.C. 154(b) by 611 days.

(21) Appl. No.: 16/535,851

(22) Filed: Aug. 8, 2019

(65) Prior Publication Data
US 2021/0038907 A1    Feb. 11, 2021

(51) Int. Cl.
G06K 9/00    (2022.01)
A61N 2/02    (2006.01)
(Continued)

(52) U.S. Cl.
CPC .................. *A61N 2/02* (2013.01); *A61N 2/06* (2013.01); *G06T 7/70* (2017.01); *G06T 7/97* (2017.01);
(Continued)

(58) Field of Classification Search
CPC . A61N 2/02; A61N 2/06; A61N 2/006; G06T 7/70; G06T 7/97;
(Continued)

(56) References Cited

U.S. PATENT DOCUMENTS 6,402,678 B1   6/2002 Fischell et al.
6,926,660 B2   8/2005 Miller
(Continued)

FOREIGN PATENT DOCUMENTS

| AU | 2007201471 B2 | 10/2008 |
|----|---|---|
| BR | PI0701434 A2 | 11/2008 |
| CA | 2582608 C | 7/2014 |
| EP | 1977787 B1 | 1/2010 |
| JP | 2008237692 A | 11/2008 |

(Continued)

OTHER PUBLICATIONS

Fukushima et al., "The Development of Magnetic Navigation System for Home Use of Repetitive Transcranial Magnetic Stimulation", Transactions of Japanese Society for Medical and Biological Engineering, Feb. 10, 2011, 49(1), 122-131.

(Continued)

*Primary Examiner* — Shervin K Nakhjavan
(74) *Attorney, Agent, or Firm* — Meunier Carlin & Curfman LLC

(57) ABSTRACT

A magnetic stimulation system may include first and second subsystems. The first subsystem may include a first stimulator, a first coil, and a first processor configured to determine stimulation parameter data for a subject. The second subsystem may include a second stimulator, a headpiece including an identifier and a second coil mounted to a headpiece body at a fixed location, an image recording device, and a second processor configured to: receive first image data for one or more first images of the subject and headpiece; receive, from the image recording device, second image data for one or more second images of the subject and headpiece; determine, using the first and second image data, that the stimulation parameter data corresponds to the subject; determine, using the second image data, that the headpiece corresponds to the subject; and determine, using the second image data, that the headpiece is at a predetermined position.

27 Claims, 10 Drawing Sheets

(51) Int. Cl.

| | |
|---|---|
| *G10L 25/51* | (2013.01) |
| *G06T 7/00* | (2017.01) |
| *G06T 7/70* | (2017.01) |
| *G06V 10/24* | (2022.01) |
| *G06V 40/60* | (2022.01) |
| *G16H 40/60* | (2018.01) |
| *A61N 2/06* | (2006.01) |
| *G16H 40/63* | (2018.01) |
| *G06F 21/60* | (2013.01) |
| *H04L 67/10* | (2022.01) |
| *A61N 2/00* | (2006.01) |

(52) U.S. Cl.
CPC ............ *G06V 10/245* (2022.01); *G06V 40/60* (2022.01); *G10L 25/51* (2013.01); *G16H 40/60* (2018.01); *G16H 40/63* (2018.01); *A61N 2/006* (2013.01); *G06F 21/602* (2013.01); *G06T 2207/30196* (2013.01); *H04L 67/10* (2013.01)

(58) Field of Classification Search
CPC ........ G06T 2207/30196; G06V 10/245; G06V 40/60; G10L 25/51; G16H 40/60; G16H 40/63; G06F 21/602; G06F 21/6245; H04L 67/10; H04L 67/025
See application file for complete search history.

(56) References Cited

U.S. PATENT DOCUMENTS

| | | | |
|---|---|---|---|
| 7,774,523 | B2 | 6/2010 | Epstein |
| 7,753,836 | B2 | 7/2010 | Peterchev |
| 8,262,556 | B2 | 9/2012 | Fischell et al. |
| 8,465,408 | B2 | 6/2013 | Phillips et al. |
| 8,480,554 | B2 | 7/2013 | Phillips et al. |
| 8,554,324 | B2 | 10/2013 | Brocke |
| 8,585,568 | B2 | 11/2013 | Phillips et al. |
| 8,740,765 | B1 | 6/2014 | Fischell et al. |
| 8,870,737 | B2 | 10/2014 | Phillips et al. |
| 8,888,672 | B2 | 11/2014 | Phillips et al. |
| 8,888,673 | B2 | 11/2014 | Phillips et al. |
| 8,926,490 | B2 | 1/2015 | Phillips et al. |
| 8,961,386 | B2 | 2/2015 | Phillips et al. |
| 9,015,057 | B2 | 4/2015 | Phillips et al. |
| 9,272,159 | B2 | 3/2016 | Phillips et al. |
| 9,308,387 | B2 | 4/2016 | Phillips et al. |
| 9,446,259 | B2 | 9/2016 | Phillips et al. |
| 9,492,680 | B2 | 11/2016 | Lu |
| 9,526,912 | B1 | 12/2016 | Fischell et al. |
| 9,649,502 | B2 | 5/2017 | Phillips et al. |
| 9,713,729 | B2 | 7/2017 | Phillips et al. |
| 9,849,300 | B2 | 12/2017 | Pascual-Leone et al. |
| 9,962,555 | B1 | 5/2018 | Charles et al. |
| 9,968,798 | B2 | 5/2018 | Fischell et al. |
| 10,004,915 | B2 * | 6/2018 | Saitoh ................... A61N 2/006 |
| 10,029,112 | B1 | 7/2018 | Fischell et al. |
| 10,065,048 | B2 | 9/2018 | Phillips et al. |
| 11,291,852 | B2 * | 4/2022 | Leuze .................... A61N 2/006 |
| 2004/0122281 | A1 | 6/2004 | Fischell et al. |
| 2008/0064950 | A1 * | 3/2008 | Ruohonen ................ G06T 7/30 |
| | | | 600/411 |
| 2008/0262287 | A1 | 10/2008 | Dussau |
| 2008/0262338 | A1 * | 10/2008 | Paitel ..................... A61B 6/037 |
| | | | 600/409 |
| 2009/0018384 | A1 | 1/2009 | Boyden et al. |
| 2009/0198144 | A1 | 8/2009 | Phillips et al. |
| 2010/0113959 | A1 | 5/2010 | Pascual-Leone et al. |
| 2010/0125312 | A1 | 5/2010 | Stevenson et al. |
| 2010/0249573 | A1 * | 9/2010 | Marks ................ G01R 33/4806 |
| | | | 600/411 |
| 2011/0213194 | A1 | 9/2011 | Fischell et al. |
| 2012/0157752 | A1 * | 6/2012 | Nishikawa ............. A61N 2/008 |
| | | | 600/15 |
| 2013/0176336 | A1 * | 7/2013 | Hannula ................ A61B 5/389 |
| | | | 345/633 |
| 2014/0042072 | A1 | 2/2014 | Sayer et al. |
| 2015/0100333 | A1 | 4/2015 | Fitzgerald et al. |
| 2016/0015588 | A1 * | 1/2016 | Tamiya ................ A61G 15/125 |
| | | | 128/845 |
| 2016/0045756 | A1 | 2/2016 | Phillips et al. |
| 2016/0235323 | A1 * | 8/2016 | Tadi ....................... A61B 5/378 |
| 2017/0087367 | A1 * | 3/2017 | Weisend ............ A61N 1/36025 |
| 2017/0113042 | A1 | 4/2017 | Goodall et al. |
| 2017/0128737 | A1 * | 5/2017 | Yasumuro ............. A61B 5/1079 |
| 2017/0151436 | A1 * | 6/2017 | Flaherty ................... A61N 7/00 |
| 2017/0296838 | A1 * | 10/2017 | Asahina ............... A61G 15/125 |
| 2017/0312536 | A1 | 11/2017 | Phillips et al. |
| 2017/0368366 | A1 | 12/2017 | Lowin |
| 2018/0126184 | A1 | 5/2018 | Phillips et al. |
| 2018/0214710 | A1 | 8/2018 | Charles et al. |
| 2018/0229049 | A1 | 8/2018 | Phillips et al. |
| 2018/0369601 | A1 * | 12/2018 | Saitoh ................... A61B 5/6803 |
| 2019/0015674 | A1 * | 1/2019 | Lowin ...................... A61N 2/02 |
| 2019/0070428 | A1 | 3/2019 | Phillips et al. |
| 2019/0111274 | A1 * | 4/2019 | Saitoh .................... A61N 2/006 |
| 2019/0231243 | A1 * | 8/2019 | Anchieta Da Silva ...................... |
| | | | A61B 5/4836 |
| 2019/0328462 | A1 * | 10/2019 | Liu ......................... G16H 40/63 |
| 2022/0062634 | A1 * | 3/2022 | Masko ................... A61N 1/3603 |
| 2022/0175326 | A1 * | 6/2022 | Solomon .................. G02C 5/006 |

FOREIGN PATENT DOCUMENTS

| | | |
|---|---|---|
| WO | 2012173618 A1 | 12/2012 |
| WO | 2015120479 A1 | 8/2015 |

OTHER PUBLICATIONS

Leuchter et al., "The Relationship Between Brain Oscillatory Activity and Therapeutic Effectiveness of Transcranial Magnetic Stimulation in the Treatment of Major Depressive Disorder", Frontiers in Human Neuroscience, Feb. 26, 2013, 7(37), 1-12.

International Search Report and Written Opinion issued for Application No. PCT/US2020/045323, dated Nov. 6, 2020.

* cited by examiner

SYSTEMS AND METHODS FOR ENABLING POINT OF CARE MAGNETIC STIMULATION THERAPY

FIELD OF THE INVENTION

The present invention relates generally to magnetic stimulation and more particularly to systems and methods for enabling point-of-care transcranial magnetic stimulation therapy.

BACKGROUND OF THE INVENTION

Various medical conditions may be treated by the application of magnetic stimulation to anatomical targets associated with specific pathologies. For example, magnetic or inductive stimulation may be used to produce a changing magnetic field that can be directed to induce an electric current in a target anatomy of a patient. Neurons, muscles, and tissue cells are forms of biological circuitry capable of carrying electrical signals and responding to electrical stimuli. When a changing magnetic field is applied to a target anatomy, an electric field is induced, causing electric current to flow in conductive portions of the anatomy. The flow of electric current stimulates biological tissue, resulting in depolarization of neurons in the tissue, which causes the neurons to be more active or less active depending on factors including pulse frequency and excitability of the target tissue. Additionally, the flow of electric current causes muscles associated with the stimulated neurons to contract. Ultimately, the induced electric current may be used to simulate desired chemical reactions in the target anatomy.

In contrast to other medical procedures for stimulating a target anatomy, magnetic stimulation may be administered in a non-invasive manner. For example, in performing transcutaneous magnetic stimulation, a magnetic field may be passed through the skin of a patient to induce an electric current in the patient's body for stimulating the target anatomy. Such magnetic stimulation may have beneficial and therapeutic biological effects in treating various portions of the body, including muscles, the spine, and the brain. Transcranial magnetic stimulation (TMS) is a non-invasive form of brain stimulation, which uses a changing magnetic field to produce an electric current in neurological tissue at a target region of the brain via electromagnetic induction. TMS therapy utilizes a stimulator connected to a magnetic coil. The magnetic coil is positioned about the patient's head at a position corresponding to the target region of the brain, and the stimulator delivers electric pulses to the magnetic coil, which induces a changing magnetic field. The magnetic field causes an electric current to be induced in the target region of the brain, resulting in stimulation of the corresponding neurological tissue. In some instances, brain stimulation may be achieved by repetitive transcranial magnetic stimulation (rTMS), which uses repetitive electromagnetic pulses applied at repetition rates that enable intended modulation effects of the cortical targets. Various neurologic or psychiatric disorders may be treated using rTMS, including, for example, major depressive disorder (MDD), bipolar disorder, anxiety, obsessive-compulsive disorder, pain (including fibromyalgia), posttraumatic stress disorder, autism spectrum disorder, and addiction. rTMS typically may be used to treat such disorders when standard treatments, such as medications, are not effective or are not well tolerated by the patient due to undesirable side effects.

TMS is currently administered to a patient by a trained clinician at a clinical facility, such as a hospital, a physician's office, or a clinic. Existing systems for performing TMS therapy generally require a patient to be evaluated and treated using the same TMS system, with close oversight of a properly trained clinician to ensure safe and compliant treatment. A course of therapy for a typical patient being treated for MDD or similar neurologic or psychiatric disorder generally requires repetitive daily treatments over a period of three to six weeks. For patients with such illnesses, frequent travel to a facility offering TMS treatment is often a hardship.

Currently, no practical TMS system exists for home or point-of-care (POC) treatment for indications, such as MDD, that require rTMS. Although portable TMS systems have been proposed, such systems do not meet all the requirements for a practical POC TMS system that can safely deliver patient-administered rTMS. Single pulse TMS devices for POC treatment of migraine have been developed and approved by certain regulatory agencies. However, use of single pulse TMS devices is not extendable to treatment of MDD and similar disorders because the treatment protocols for such disorders require repetitive application of much higher power magnetic field pulses, which in turn necessitates greater attention to management of safety risks and higher system power requirements. Other TMS devices have been developed for POC treatment of certain neurological disorders, which use rotating magnets to produce low level magnetic field pulses. Such sub-threshold devices, however, have not been demonstrated to be as effective for treatment of MDD and similar disorders as rTMS administered above stimulation threshold. In sum, current technology does not enable patient-administered POC TMS treatment for indications that require rTMS because existing TMS systems lack the required portability or functionality and/or fail to address the necessary safety and regulatory requirements.

A need therefore exists for improved systems and methods for enabling point-of-care magnetic stimulation therapy to alleviate the burden on patients with neurologic or psychiatric disorders that require repetitive transcranial magnetic stimulation.

SUMMARY OF THE INVENTION

The present invention provides systems and methods for performing transcutaneous magnetic stimulation to treat a subject. In one aspect, a system for performing transcutaneous magnetic stimulation to treat a subject is provided. In one embodiment, the system includes a first subsystem and a second subsystem in communication with the first subsystem. The first subsystem includes at least one first memory that stores first computer-executable instructions, at least one first processor, a first stimulator, a first magnetic coil, and a first user interface. The first stimulator is in communication with the at least one first processor and configured to generate electric pulses. The first magnetic coil is in communication with the first stimulator and configured to deliver magnetic stimulation to a first subject. The first user interface is in communication with the at least one first processor and configured to receive user inputs related to the magnetic stimulation delivered by the first magnetic coil to the first subject. The at least one first processor is configured to access the at least one first memory and execute the first computer-executable instructions to: determine first subject data associated with the first subject, the first subject data including one or more subject identifiers associated with the first subject; determine, based at least in part on one or more indications of user input from the first user interface, first stimulation parameter data including one or more first parameters associated with operation of the first stimulator or the first magnetic coil for the first subject; and cause the first subject data and the first stimulation parameter data to be stored in association with one another. The second subsystem includes at least one second memory that stores second computer-executable instructions, at least one second processor, a second stimulator, a headpiece, and an image recording device. The second stimulator is in communication with the at least one second processor and configured to generate electric pulses. The headpiece is configured to engage a head of the first subject and includes one or more headpiece identifiers associated with the headpiece, and a second magnetic coil in communication with the second stimulator and configured to deliver magnetic stimulation to the first subject. The second magnetic coil is mounted to a body of the headpiece at a fixed, prescribed location by a secure locking means that can only be released or altered by an authorized person. The image recording device is in communication with the at least one second processor and configured to capture images of the first subject and the headpiece. The at least one second processor is configured to access the at least one second memory and execute the second computer-executable instructions to: receive the first subject data and the first stimulation parameter data; receive first image data associated with the first subject data and the first stimulation parameter data, the first image data corresponding to one or more first images of at least a portion of the first subject and at least a portion of the headpiece; receive second image data from the image recording device, the second image data corresponding to one or more second images of at least a portion of the first subject and at least a portion of the headpiece; determine, based at least in part on the first image data and the second image data, that the first stimulation parameter data is associated with the first subject; and determine, based at least in part on the second image data, that the headpiece is associated with the first subject.

In some embodiments, the one or more first parameters includes at least one of: (i) a magnitude and a timing sequence of electric pulses to be generated by the second stimulator, (ii) a magnitude of magnetic stimulation to be delivered by the second magnetic coil, and (iii) a position of the headpiece relative to a target anatomy of the first subject.

In some embodiments, the at least one second processor is further configured to enable operation of the second stimulator or the second magnetic coil based at least in part on the determination that the headpiece is associated with the first subject.

In some embodiments, the second subsystem further includes a data storage in communication with the at least one second processor, and the at least one second processor is further configured to receive the first subject data, the first stimulation parameter data, and the first image data from the data storage, the first subject data, the first stimulation parameter data, and the first image data being encrypted.

In some embodiments, the second subsystem further includes a data storage in communication with the at least one second processor, and the at least one second processor is further configured to: receive the first subject data, the first stimulation parameter data, and the first image data from the first subsystem or a remote server via one or more networks, the first subject data, the first stimulation parameter data, and the first image data being encrypted; and cause the first subject data, the first stimulation parameter data, and the first image data to be stored in association with one another at the data storage.

In some embodiments, the second subsystem further includes a data storage in communication with the at least one second processor, and the at least one second processor is further configured to: receive second stimulation parameter data from the first subsystem, a remote server, or a user device associated with a supervising clinician via one or more networks, the second stimulation parameter data being encrypted and including one or more second parameters associated with operation of the second stimulator or the second magnetic coil for the first subject; determine that the second stimulation parameter data supersedes at least a portion of the first stimulation parameter data; and cause the second stimulation parameter data to be stored in association with the first subject data and the first image data at the data storage.

In some embodiments, the second subsystem further includes a data storage in communication with the at least one second processor, and the at least one second processor is further configured to: send stimulation history data to the first subsystem, a remote server, or a user device associated with a supervising clinician via one or more networks, the stimulation history data being encrypted and including one or more metrics associated with one or more stimulation sessions administered to the first subject; receive second stimulation parameter data from the first subsystem, the remote server, or the user device via the one or more networks, the second stimulation parameter data being encrypted and including one or more second parameters associated with operation of the second stimulator or the second magnetic coil for the first subject; determine that the second stimulation parameter data supersedes at least a portion of the first stimulation parameter data; and cause the second stimulation parameter data to be stored in association with the first subject data and the first image data at the data storage.

In some embodiments, the second subsystem further includes an audio recording device in communication with the at least one second processor and configured to capture audio recordings of the first subject, and the at least one second processor is further configured to: receive first audio data, the first audio data corresponding to one or more first audio recordings of the first subject; receive second audio data from the audio recording device, the second audio data corresponding to one or more second audio recordings of the first subject; and determine, based at least in part on the first image data, the second image data, the first audio data, and the second audio data, that the first stimulation parameter data is associated with the first subject.

In some embodiments, the second subsystem further includes an audio recording device in communication with the at least one second processor and configured to capture audio recordings of the first subject, and the at least one second processor is further configured to: receive first audio data, the first audio data corresponding to one or more first audio recordings of the first subject; cause the second stimulator to assume a first operational state; receive second audio data from the audio recording device, the second audio data corresponding to one or more second audio recordings of the first subject and being indicative of a first command associated with a second operational state of the second stimulator; determine, based at least in part on the first audio data, that the second audio data is associated with the first subject; and cause the second stimulator to assume the second operational state based at least in part on the determination that the second audio data is associated with the first subject.

In some embodiments, the at least one second processor is further configured to: receive third audio data from the audio recording device, the third audio data corresponding to one or more third audio recordings of a second subject and being indicative of a second command associated with a third operational state of the second stimulator; determine, based at least in part on the first audio data, that the third audio data is not associated with the first subject; and cause the second stimulator to maintain the second operational state based at least in part on the determination that the third audio data is not associated with the first subject.

In some embodiments, the one or more second images includes at least a portion of the one or more headpiece identifiers, and the at least one second processor is further configured to determine, based at least in part on the at least a portion of the one or more headpiece identifiers, that the headpiece is associated with the first subject.

In some embodiments, the one or more headpiece identifiers includes an encrypted identifier comprising at least one of: (i) a barcode, (ii) a radio frequency identification tag, and (iii) a structural pattern.

In some embodiments, the one or more first parameters includes a pre-determined position of the headpiece relative to a target anatomy of the first subject, and the fixed location of the second magnetic coil corresponds to the pre-determined position of the headpiece relative to the target anatomy of the first subject.

In some embodiments, the at least one second processor is further configured to determine, at one or more times prior to or during a treatment session and based at least in part on the second image data, that the headpiece is at the pre-determined position relative to the target anatomy of the first subject.

In some embodiments, the second subsystem further includes a first indicator in communication with the at least one second processor, and the at least one second processor is further configured to cause activation of the first indicator based at least in part on the determination that the headpiece is at the pre-determined position relative to the target anatomy of the first subject.

In some embodiments, the second subsystem further includes a second indicator in communication with the at least one second processor, and the at least one second processor is further configured to: receive third image data from the image recording device, the third image data corresponding to one or more third images of at least a portion of the first subject and at least a portion of the headpiece; determine, based at least in part on the third image data, that the headpiece is not at the pre-determined position relative to the target anatomy of the first subject; and cause activation of the second indicator based at least in part on the determination that the headpiece is not at the pre-determined position, the second indicator being indicative of a movement of the headpiece relative to the head of the first subject toward the pre-determined position relative to the target anatomy of the first subject.

In some embodiments, the first indicator and the second indicator are mounted to the body of the headpiece.

In some embodiments, the image recording device is mounted to the body of the headpiece.

In some embodiments, the second subsystem further includes a mirror configured to reflect light, and the one or more second images includes the at least a portion of the first subject and the at least a portion of the headpiece reflected by the mirror.

In some embodiments, the at least one second processor is further configured to: receive third image data from the image recording device, the third image data corresponding to one or more third images of at least a portion of the first subject; determine, based at least in part on the third image data, a state of the first subject, the state of the first subject including one of: (i) an awake state, (ii) an asleep state, and (iii) a seizure state; and enable or disable operation of the second stimulator or the second magnetic coil based at least in part on the state of the first subject.

In some embodiments, the state of the first subject includes the asleep state, the second subsystem further includes an alarm in communication with the at least one second processor, and the at least one second processor is further configured to cause activation of the alarm based at least in part on the state of the first subject.

In some embodiments, the state of the first subject includes the seizure state, and the at least one second processor is further configured to: disable operation of the second stimulator or the second magnetic coil based at least in part on the state of the first subject; and send an emergency message to the first subsystem, a user device associated with a supervising clinician, or a user device associated with an emergency response service based at least in part on the state of the first subject, the emergency message being indicative of the seizure state.

In some embodiments, the second subsystem further includes a second user interface in communication with the at least one second processor, and the at least one second processor is further configured to: cause the second stimulator to assume a first operational state; receive an indication of interaction by the first subject with the second user interface, the indication of interaction being associated with a second operational state of the second stimulator; and cause the second stimulator to assume the second operational state based at least in part on the indication of interaction.

In some embodiments, the second subsystem is portable and configured for use at a remote location relative to the first subsystem.

In another aspect, a method for performing transcutaneous magnetic stimulation to treat a subject is provided. In one embodiment, the method includes: determining, by at least one first processor coupled to at least one first memory of a first subsystem, first subject data associated with a first subject, the first subject data including one or more subject identifiers associated with the first subject; causing, by the at least one first processor, a first stimulator of the first subsystem to generate a first plurality of electric pulses; causing, by the at least one first processor, a first magnetic coil of the first subsystem to deliver first magnetic stimulation to the first subject; determining, by the at least one first processor and based at least in part on one or more indications of user input from a first user interface of the first subsystem, first stimulation parameter data including one or more first parameters associated with operation of the first stimulator or the first magnetic coil for the first subject; causing, by the at least one first processor, the first subject data and the first stimulation parameter data to be stored in association with one another; receiving, by at least one second processor coupled to at least one second memory of a second subsystem, the first subject data and the first stimulation parameter data; receiving, by the at least one second processor, first image data associated with the first subject data and the first stimulation parameter data, the first image data corresponding to one or more first images of at least a portion of the first subject and at least a portion of a headpiece, the headpiece including one or more headpiece identifiers associated with the headpiece; receiving, by the at least one second processor, second image data from an image recording device of the second subsystem, the second image data corresponding to one or more second images of at least a portion of the first subject and at least a portion of the headpiece; determining, by the at least one second processor and based at least in part on the first image data and the second image data, that the first stimulation parameter data is associated with the first subject; determining, by the at least one second processor and based at least in part on the second image data, that the headpiece is associated with the first subject; and enabling, by the at least one second processor and based at least in part on the determination that the headpiece is associated with the first subject, operation of a second stimulator of the second subsystem or a second magnetic coil of the headpiece, the second stimulator being configured to generate electric pulses, and the second magnetic coil being mounted to a body of the headpiece at a fixed location by a secure locking means and configured to deliver magnetic stimulation to the first subject.

In some embodiments, the method further includes: sending, by the at least one second processor, stimulation history data to the first subsystem, a remote server, or a user device associated with a supervising clinician via one or more networks, the stimulation history data being encrypted and including one or more metrics associated with one or more stimulation sessions administered to the first subject; receiving, by the at least one second processor, second stimulation parameter data from the first subsystem, the remote server, or the user device via the one or more networks, the second stimulation parameter data being encrypted and including one or more second parameters associated with operation of the second stimulator or the second magnetic coil for the first subject; determining that the second stimulation parameter data supersedes at least a portion of the first stimulation parameter data; and causing the second stimulation parameter data to be stored in association with the first subject data and the first image data at a data storage of the second subsystem.

In some embodiments, the method further includes: causing, by the at least one second processor, the second stimulator to assume a first operational state; receiving, by the at least one second processor, an indication of interaction by the first subject with a second user interface of the second subsystem, the indication of interaction being associated with a second operational state of the second stimulator; and causing, by the at least one second processor and based at least in part on the indication of interaction, the second stimulator to assume the second operational state.

These and other aspects and improvements of the present disclosure will become apparent to one of ordinary skill in the art upon review of the following detailed description when taken in conjunction with the several drawings and the appended claims.

BRIEF DESCRIPTIONS OF THE DRAWINGS

FIG. 1A illustrates an example architecture of a magnetic stimulation system for managing and performing magnetic stimulation to treat a subject and an example process flow diagram in accordance with one or more embodiments of the disclosure.

FIG. 1B schematically illustrates an example architecture of a prescribing system for determining a magnetic stimulation prescription for a subject in accordance with one or more embodiments of the disclosure.

FIG. 1C illustrates an example implementation of a prescribing system for determining a magnetic stimulation prescription for a subject in accordance with one or more embodiments of the disclosure.

FIG. 1D schematically illustrates an example architecture of a treatment system for administering magnetic stimulation to a subject in accordance with one or more embodiments of the disclosure.

Figure 1A:
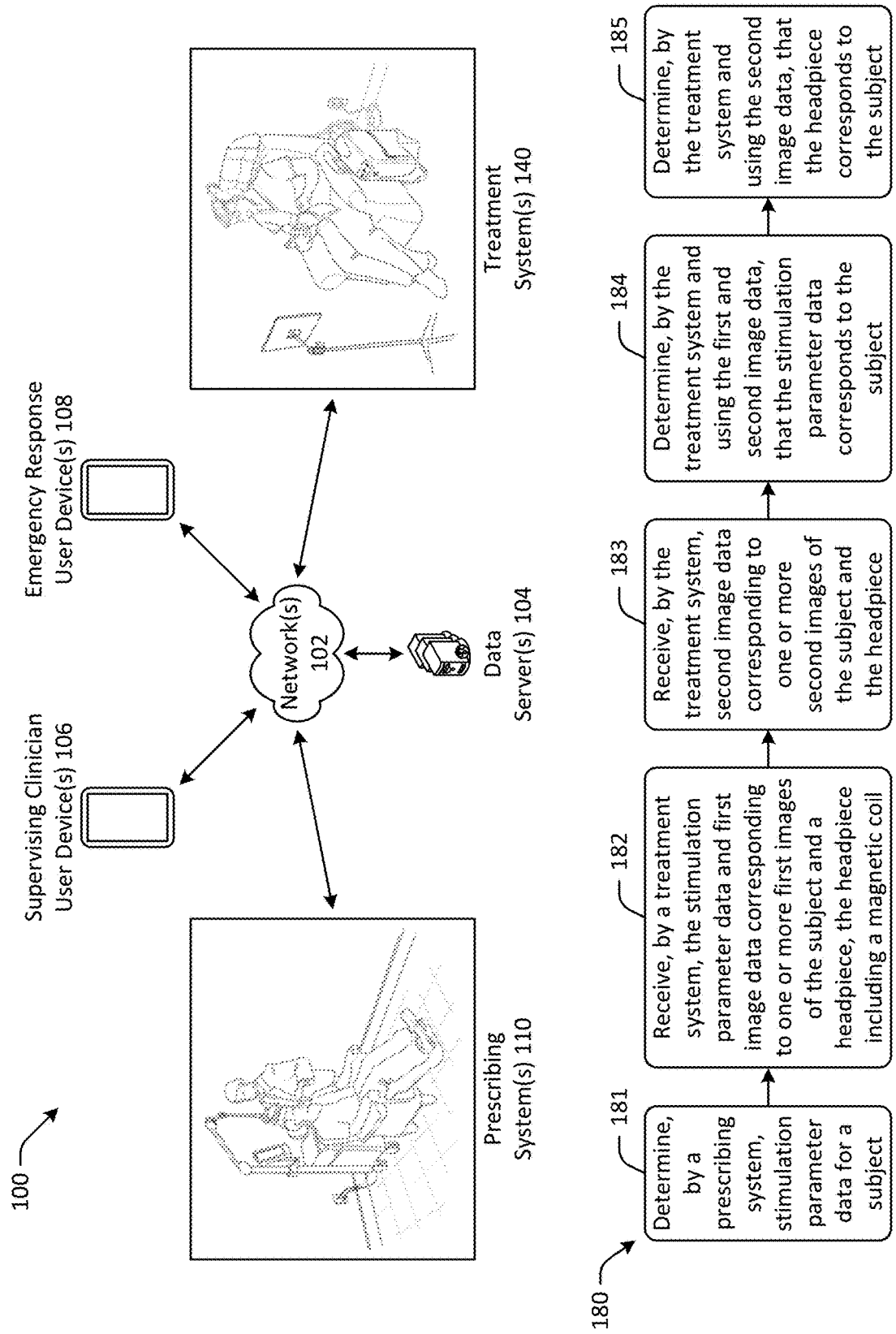
FIG. 1E illustrates an example implementation of a treatment system for administering magnetic stimulation to a subject in accordance with one or more embodiments of the disclosure.
FIG. 1F illustrates an example implementation of a portion of the treatment system of FIG. 1E.

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. The use of the same reference numerals indicates similar, but not necessarily the same or identical components. Different reference numerals may be used to identify similar components. Various embodiments may utilize elements or components other than those illustrated in the drawings, and some elements and/or components may not be present in various embodiments. The use of singular terminology to describe a component or element may, depending on the context, encompass a plural number of such components or elements and vice versa.

DETAILED DESCRIPTION OF THE INVENTION

In the following description, specific details are set forth describing some embodiments consistent with the present invention. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances, well known methods, procedures, components, and circuits have not been described in detail so as not to unnecessarily obscure aspects of the embodiments.

Embodiments of magnetic stimulation systems and methods for using such systems for performing magnetic stimulation to treat a subject (i.e., a patient) are provided. As described herein, the magnetic stimulation system is configured for managing and performing magnetic stimulation to treat a subject. In some embodiments, the magnetic stimulation system is configured for managing and performing transcutaneous magnetic stimulation, such as transcranial magnetic stimulation (TMS) or repetitive transcranial magnetic stimulation (rTMS). As described herein, the magnetic stimulation system advantageously enables point-of-care (POC) magnetic stimulation therapy to alleviate the burden on subjects with neurologic or psychiatric disorders that require rTMS. In particular, the magnetic stimulation system addresses the necessary functional, safety, and regulatory requirements for enabling subject-administered POC TMS treatment for indications that require rTMS. For example, according to embodiments described herein, the magnetic stimulation system may address one or more, or all, of the following: providing true portability of a treatment system for administering TMS to a patient; securely guaranteeing that the proper subject is being treated by the treatment system; guaranteeing that a magnetic coil of the treatment system is properly positioned on the subject for a duration of a treatment session and that the subject remains in an optimal posture; securely guaranteeing that a treatment protocol followed by the treatment system is the proper prescription for the subject and cannot be altered without approval of a supervising clinician; monitoring the subject throughout a treatment session for onset of sleep, seizure, or other state and taking proper responsive action in the event of non-compliance with performance criteria; and providing user interfaces for clinicians and subjects which are adapted to the expertise and training levels of the intended user. In this manner, the magnetic stimulation system addresses certain functional, safety, and regulatory concerns associated with subject-administered POC TMS treatment.

Referring now to FIG. 1A, a magnetic stimulation system 100 in accordance with one or more embodiments of the disclosure is depicted. The magnetic stimulation system 100 is configured for managing and performing magnetic stimulation to treat a subject. The magnetic stimulation system 100 generally includes at least one prescribing system 110 (also referred to herein as a "first subsystem") and at least one treatment system 140 (also referred to herein as a "second subsystem") in communication with one another. Although only a single prescribing system 110 and a single treatment system 140 are depicted in FIG. 1A, the magnetic stimulation system 100 may include any number of the prescribing systems 110 and the treatment systems 140. In some embodiments, a single prescribing system 110 associated with a particular clinical location may be able to communicate with a plurality of treatment systems 140 associated with different subjects. In some embodiments, a single treatment system 140 associated with a particular subject may be able to communicate with a plurality of prescribing systems 110 associated with different clinical locations. The prescribing system 110 is configured for use in determining a magnetic stimulation prescription for a subject and performing additional functions described herein. The treatment system 140 is configured for use in administering magnetic stimulation to a subject and performing additional functions described herein. The treatment system 140 is portable and configured for use at a remote location relative to the prescribing system 110. The prescribing system 110 may be used at a clinical facility, such as a hospital, a physician's office, or a clinic by a trained clinician. In contrast, the treatment system 140 may be setup and customized for a subject at a clinical facility and then transported to the subject's home or other convenient location remote from the prescribing system 110 for therapy administered by the subject or an assistant having only minimal clinical training. Because the prescribing system 110, not the treatment system 140, is used to evaluate a subject and determine the subject's magnetic stimulation prescription, the treatment system 140 need not include the complex components and software required for such functions. Accordingly, the treatment system 140 may be provided as a compact, portable system including only the components and software required for administering magnetic stimulation and performing additional functions described herein. The treatment system 140 also may use power efficient topologies to further enhance portability of the treatment system 140. Because the treatment system 140, not the prescribing system 110, is used to administer magnetic stimulation therapy, such as rTMS therapy, the prescribing system 110 need not include the components and software required for such functions. Accordingly, the prescribing system 110 may include only a single pulse stimulator that is smaller than that required for TMS therapy and may be incapable of administering TMS therapy.

As shown in FIG. 1A, the prescribing system 110 and the treatment system 140 are in communication with one another via one or more network(s) 102. In this manner, the prescribing system 110 and the treatment system 140 may send data to and receive data from one another as well as other systems, devices, and/or servers connected to the network(s) 102. The network(s) 102 may include, but are not limited to, any one or more different types of communications networks such as, for example, cable networks, public networks (e.g., the Internet), private networks (e.g., frame-relay networks), wireless networks, cellular networks, telephone networks (e.g., a public switched telephone network), or any other suitable private or public packet-switched or circuit-switched networks. Further, the network(s) 102 may have any suitable communication range associated therewith and may include, for example, global networks (e.g., the Internet), metropolitan area networks (MANs), wide area networks (WANs), local area networks (LANs), or personal area networks (PANs). In addition, the network(s) 102 may include communication links and associated networking devices (e.g., link-layer switches, routers, etc.) for transmitting network traffic over any suitable type of medium including, but not limited to, coaxial cable, twisted-pair wire (e.g., twisted-pair copper wire), optical fiber, a hybrid fiber-coaxial (HFC) medium, a microwave medium, a radio frequency communication medium, a satellite communication medium, or any combination thereof.

In the example of FIG. 1A, the magnetic stimulation system 100 also includes one or more data server(s) 104 in communication with the prescribing system 110 and the treatment system 140 via the network(s) 102. The data server(s) 104 are configured for storing various types of data related to managing and performing magnetic stimulation, including, but not limited to, subject data, stimulation parameter data, stimulation history data, security data, image data, audio data, medical records data, billing data, and the like for one or more subjects being treated by the magnetic stimulation system 100. As described below, the prescribing system 110 and the treatment system 140 may send data to and receive data from the data server(s) 104 via the network(s) 102. The data server(s) 104 may be configured in a conventional manner for storing data.

In some embodiments, the magnetic stimulation system 100 also includes one or more user devices in communication with the prescribing system 110, the treatment system 140, and the data server(s) 104 via the network(s) 102. For example, as shown in FIG. 1A, the magnetic stimulation system 100 includes one or more supervising clinician user device(s) 106 and one or more emergency response user device(s) 108. Each supervising clinician user device 106 is associated with a clinician supervising magnetic stimulation treatment for one or more subjects. As described below, the supervising clinician user device 106 may be used by the clinician to send data to and receive data from the prescribing system 110, the treatment system 140, and the data server(s) 104 via the network(s) 102. For example, the supervising clinician user device 106 may be used to receive stimulation history data for a subject and modify stimulation parameter data for the subject. In this manner, the supervising clinician may use the user device 106 to remotely monitor magnetic stimulation treatment of the subject, determine compliance with a treatment protocol for the subject, modify the treatment protocol, monitor potential adverse events, determine an appropriate response to an adverse event, disable operation of the treatment system 140, and the like. Each emergency response user device 108 is associated with an emergency response service. As described below, the emergency response user device 108 may be used by the emergency response service to send data to and receive data from the treatment system 140 via the network(s) 102. For example, the emergency response user device 108 may be used to receive an emergency message indicative of an adverse event, such as a subject being in a seizure state, from the treatment system 140 and send a response message indicating that emergency response personnel are being dispatched to the location of the treatment system 140. In this manner, the emergency response service may use the user device 108 to remotely determine occurrence of an adverse event, initiate an appropriate response to an adverse event, and the like. The supervising clinician user device 106 and the emergency response user device 108 may be any type of electronic device, such as a mobile phone, a tablet computer, a laptop computer, a desktop computer, and the like, used by a user to communicate with other systems, devices, and/or servers of the magnetic stimulation system 100.

Figure 1B:
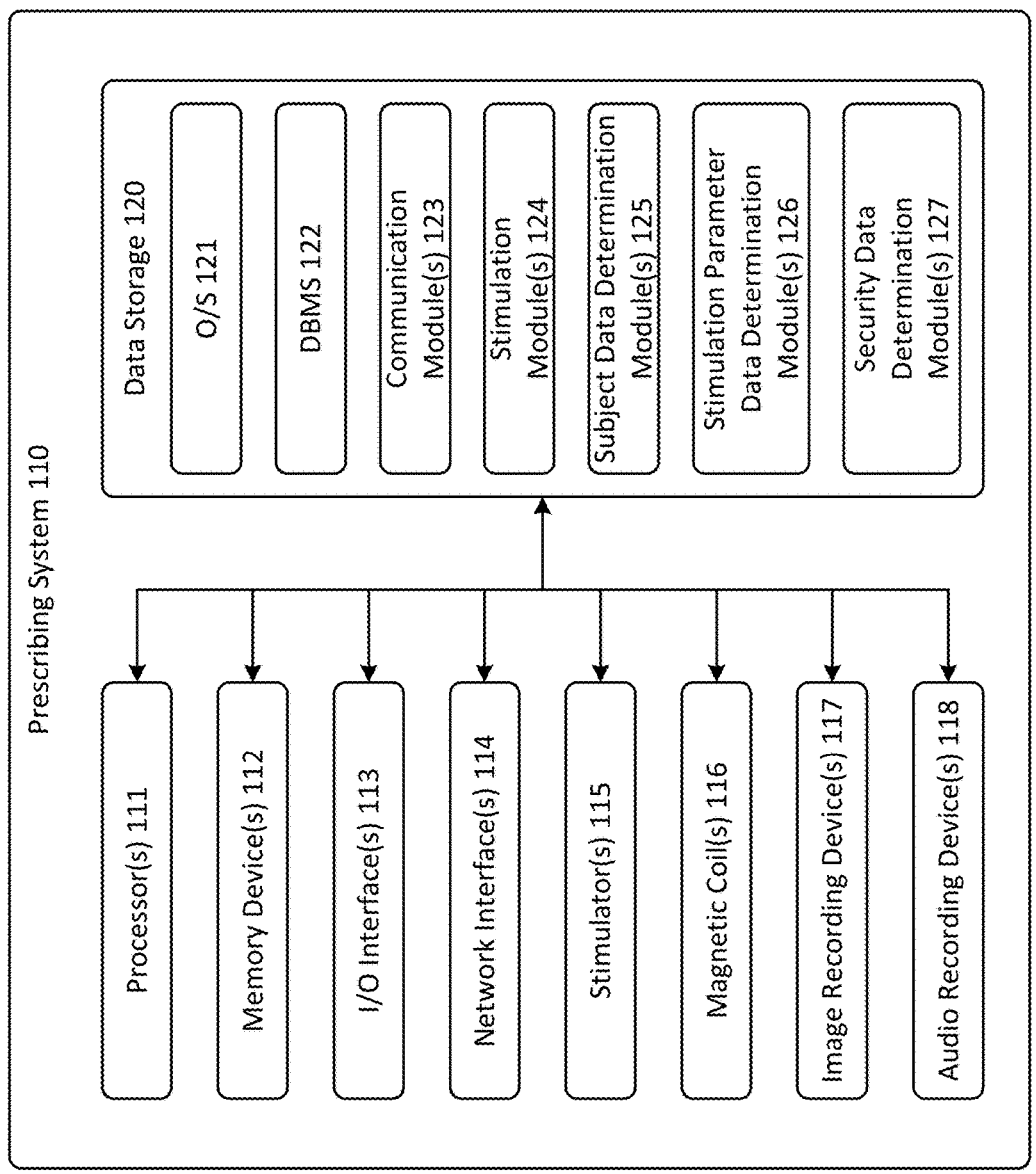

FIG. 1B illustrates an example architecture of the prescribing system 110. As shown, the prescribing system 110 includes one or more processor(s) 111, one or more memory device(s) 112 (also referred to herein as "memory"), one or more input/output (I/O) interface(s) 113, one or more network interface(s) 114, one or more stimulator(s) 115, one or more magnetic coil(s) 116, one or more image recording device(s) 117, one or more audio recording device(s) 118, and data storage 120. The prescribing system 110 also includes one or more bus(es) that functionally couple the various components of the prescribing system 110. The bus(es) may include at least one of a system bus, a memory bus, an address bus, or a message bus permitting the exchange of information (e.g., data (including computer-executable code), signaling, etc.) between the various components of the prescribing system 110.

The memory 112 of the prescribing system 110 may include volatile memory (memory that maintains its state when supplied with power), such as random access memory (RAM), and/or non-volatile memory (memory that maintains its state even when not supplied with power), such as read-only memory (ROM), flash memory, ferroelectric RAM (FRAM), and so forth. The data storage 120 may include removable storage and/or non-removable storage including, but not limited to, magnetic storage, optical disk storage, and/or tape storage. The data storage 120 may provide non-volatile storage of computer-executable instructions and other data. The memory 112 and the data storage 120, removable and/or non-removable, are examples of computer-readable storage media (CRSM) as that term is used herein.

The processor(s) 111 are configured to access the memory 112 and execute computer-executable instructions loaded therein. For example, the processor(s) 111 may be configured to execute computer-executable instructions of the various program modules, applications, engines, or the like of the prescribing system 110 to cause or facilitate various operations to be performed in accordance with embodiments of the disclosure. The processor(s) 111 may include any suitable processing unit capable of accepting data as input, processing the input data in accordance with stored computer-executable instructions, and generating output data.

The I/O interface(s) 113 facilitates the receipt of input information by the prescribing system 110 from one or more I/O devices as well as the output of information from the prescribing system 110 to the one or more I/O devices. The I/O devices may include any of a variety of components, such as a display or display screen having a touch surface or touchscreen, an audio output device for producing sound, such as a speaker, an audio recording or capture device, such as a microphone, an image and/or video recording or capture device, such as a camera, a haptic unit, and so forth. The I/O interface(s) 113 also may include an interface for an external peripheral device connection such as universal serial bus (USB), FireWire, Thunderbolt, Ethernet port or other connection protocol that may connect to the network(s) 102. The I/O interface(s) 113 also may include a connection to one or more of the antenna(e) to connect to the network(s) 102 via a wireless local area network (WLAN) (such as Wi-Fi) radio, Bluetooth, and/or a wireless network radio, such as a radio capable of communication with a wireless communication network such as a Long Term Evolution (LTE) network, a WiMAX network, a 3G network, etc. The network interface(s) 114 communicates with any of a variety of other systems, platforms, networks, devices, and so forth. The network interface(s) 114 may enable communication, for example, with one or more wireless routers, one or more host servers, one or more web servers, and the like via the network(s) 102.

The stimulator(s) 115 is configured to generate electric pulses suitable for magnetic stimulation, such as transcutaneous magnetic stimulation, transcranial magnetic stimulation, repetitive transcranial magnetic stimulation, and the like. The stimulator(s) 115 may be any type of pulse generator configured in a conventional manner. The magnetic coil(s) 116 is configured to deliver magnetic stimulation, such as transcutaneous magnetic stimulation, transcranial magnetic stimulation, repetitive transcranial magnetic stimulation, and the like, to a subject. The magnetic coil(s) 116 may be any type of suitable coil configured in a conventional manner. The image recording device(s) 117 is configured to capture images and generate image data corresponding to captured images. In some embodiments, the image recording device(s) 117 also is configured to capture videos and generate video data corresponding to captured videos. The image recording device(s) 117 may be any type of suitable device, such as a camera, for capturing images and/or videos. The audio recording device(s) 118 is configured to capture audio recordings and generate audio data corresponding to captured audio recordings. The audio recording device(s) 118 may be any type of suitable device, such as a microphone, for capturing audio recordings.

As shown in FIG. 1B, the data storage 120 stores one or more operating systems (O/S) 121, one or more database management systems (DBMS) 122, and one or more program module(s), applications, engines, computer-executable code, scripts, or the like, such as, for example, one or more communication module(s) 123, one or more stimulation module(s) 124, one or more subject data determination module(s) 125, one or more stimulation parameter determination module(s) 126, and one or more security data determination module(s) 127. Some or all of these modules may be or include sub-modules. It should be appreciated that the program modules depicted in FIG. 1B as being stored in the data storage 120 are merely illustrative and not exhaustive and that the processing described as being supported by any particular module may alternatively be distributed across multiple modules or performed by a different module. Any of the components depicted as being stored in the data storage 120 may include any combination of software, firmware, and/or hardware. The software and/or firmware may include computer-executable code, instructions, or the like that may be loaded into the memory 112 for execution by one or more of the processor(s) 111. Any of the components depicted as being stored in data storage 120 may support the functionality described in reference to the corresponding components named herein. The O/S 121 may be loaded from the data storage 120 into the memory 112 and provide an interface between software executing on the prescribing system 110 and the hardware resources of the prescribing system 110. The DBMS 122 may be loaded into the memory 112 and support functionality for accessing, retrieving, storing, and/or manipulating data stored in the memory 112 and/or data stored in the data storage 120.

The communication module(s) 123 includes computer-executable instructions, code, or the like that, responsive to execution by one or more of the processor(s) 111 perform functions including, but not limited to, communicating with remote servers, communicating with remote datastores, communicating with other electronic devices, sending or receiving information and instructions, and the like. The stimulation module(s) 124 includes computer-executable instructions, code, or the like that, responsive to execution by one or more of the processor(s) 111 perform functions including, but not limited to, causing the stimulator(s) 115 to generate electric pulses, causing the magnetic coil(s) 116 to deliver magnetic stimulation to a subject, and the like. The subject data determination module(s) 125 includes computer-executable instructions, code, or the like that, responsive to execution by one or more of the processor(s) 111 perform functions including, but not limited to, receiving indications of user input from a user interface, determining subject data based at least in part on such indications, and the like. The stimulation parameter determination module(s) 126 includes computer-executable instructions, code, or the like that, responsive to execution by one or more of the processor(s) 111 perform functions including, but not limited to, receiving indications of user input from a user interface, determining stimulation parameter data based at least in part on such indications, and the like. The security data determination module(s) 127 includes computer-executable instructions, code, or the like that, responsive to execution by one or more of the processor(s) 111 perform functions including, but not limited to, receiving image data from the image recording device(s) 117, receiving audio data from the audio recording device(s) 118, and determining security data based at least in part on the image data and/or the audio data, and the like.

Figure 1C:
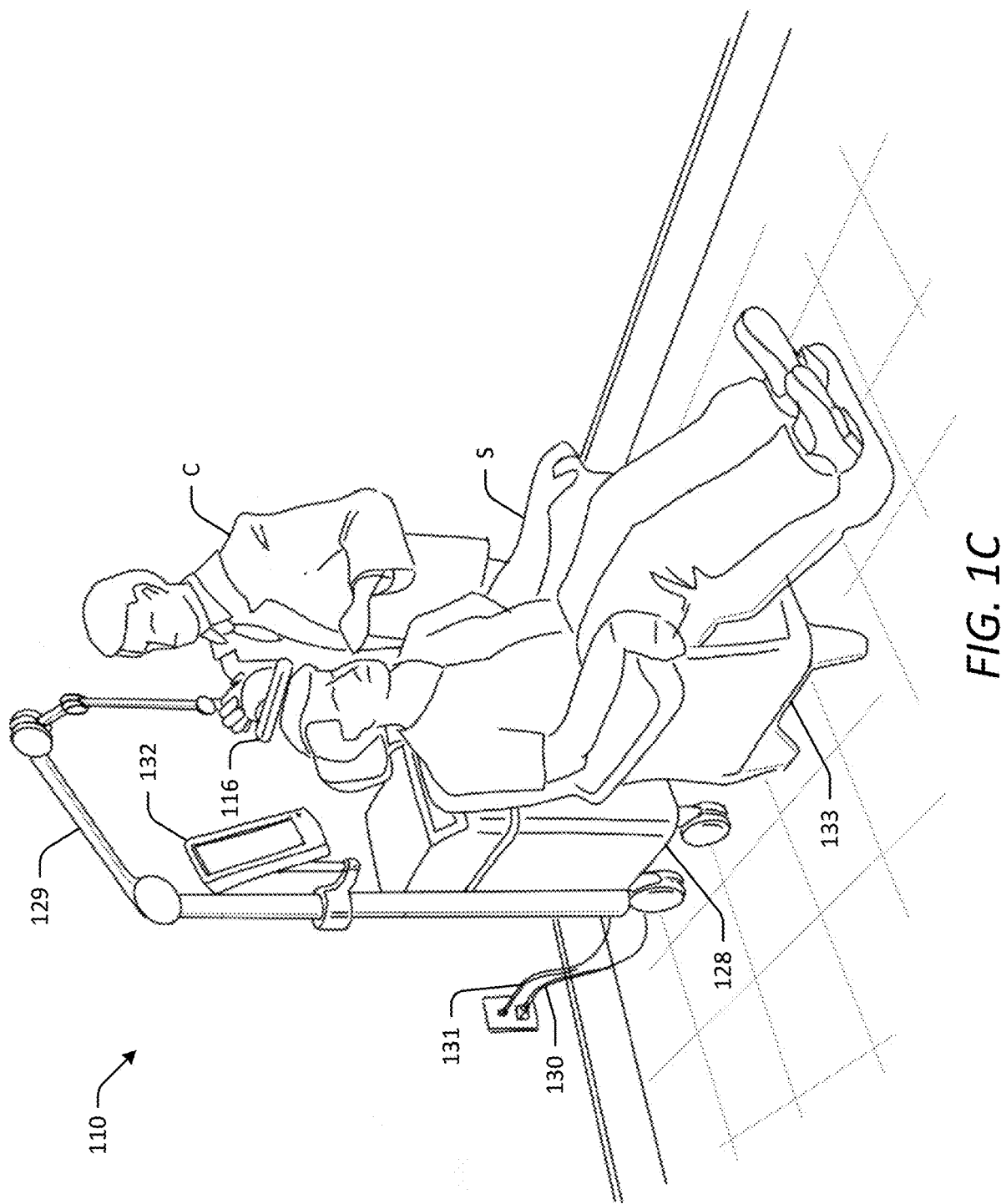

FIG. 1C illustrates an example implementation of the prescribing system 110. As shown, the prescribing system 110 includes an electronics unit 128, a support arm 129, a power cable 130, a network cable 131, a user interface 132, and a chair 133. The electronics unit 128 may include one or more, or all, of the processor(s) 111, the memory device(s) 112, the I/O interface(s) 113, the network interface(s) 114, the stimulator(s) 115, the image recording device(s) 117, the audio recording device(s) 118, and the data storage 120 described above. For example, such components may be contained within a housing of the electronics unit 128 or mounted thereon. As shown, the magnetic coil(s) 116 is mounted to the support arm 129. The support arm 129 may be an articulating arm configured to allow a clinician C to move the magnetic coil(s) 116 about the head of a subject S during use of the prescribing system 110. The power cable 130 extends from the electronics unit 128 and facilitates transmission of power from a power source (e.g., mains power) to the various components of the prescribing system 110. The network cable 131 extends from the electronics unit 128 and facilitates communication between the prescribing system 110 and the network(s) 102. The chair 133 is configured for positioning the subject S in an optimal posture for performing magnetic stimulation.

Figure 1D:
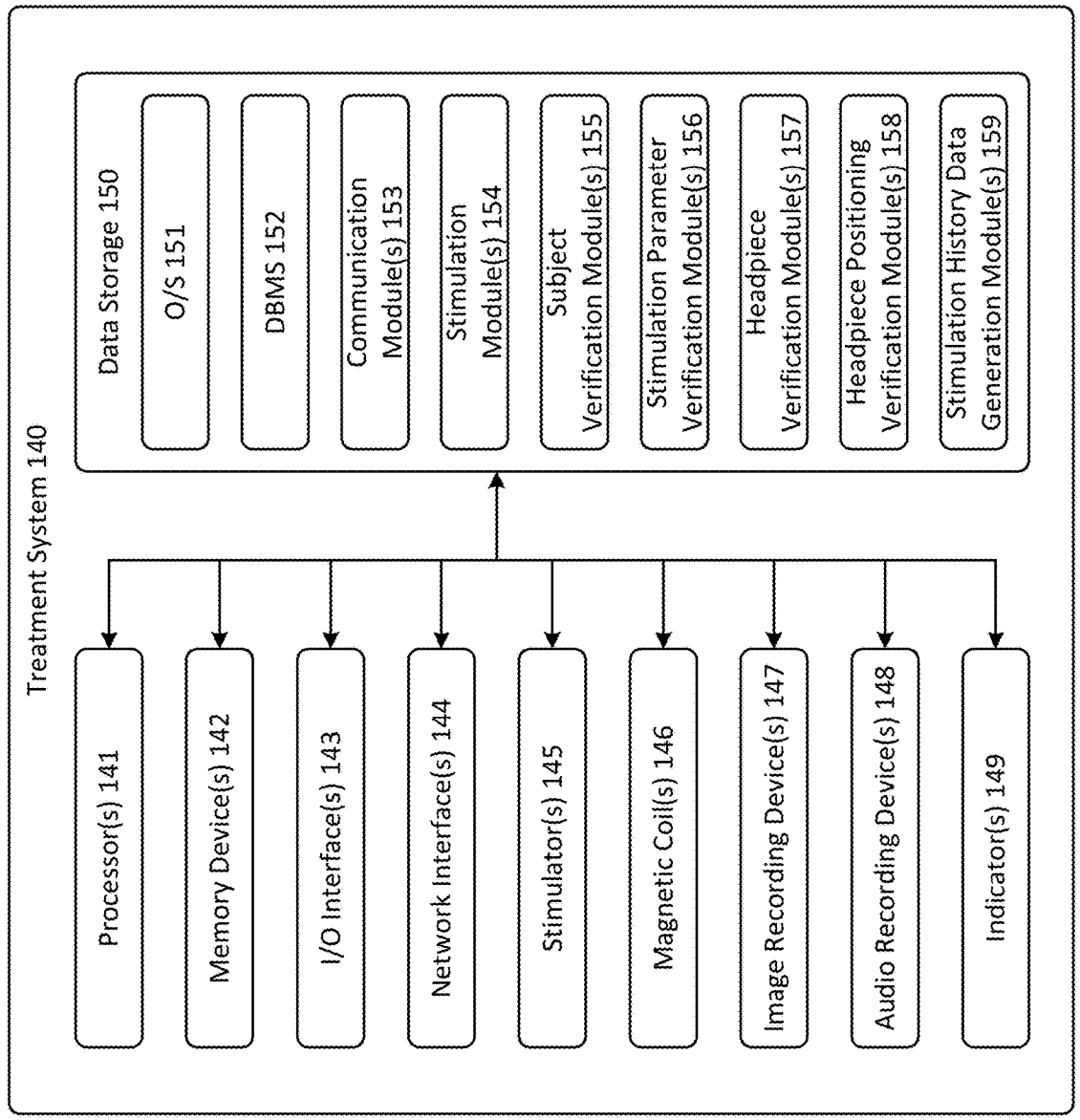

FIG. 1D illustrates an example architecture of the treatment system 140. As shown, the treatment system 140 includes one or more processor(s) 141, one or more memory device(s) 142 (which also referred to herein as "memory"), one or more input/output (I/O) interface(s) 143, one or more network interface(s) 144, one or more stimulator(s) 145, one or more magnetic coil(s) 146, one or more image recording device(s) 147, one or more audio recording device(s) 148, one or more indicator(s) 149, and data storage 150. The treatment system 140 also includes one or more bus(es) that functionally couple the various components of the treatment system 140. The bus(es) may include at least one of a system bus, a memory bus, an address bus, or a message bus permitting the exchange of information (e.g., data (including computer-executable code), signaling, etc.) between the various components of the treatment system 140. The processor(s) 141, the memory device(s) 142, the I/O interface(s) 143, the network interface(s) 144, the stimulator(s) 145, the magnetic coil(s) 146, the image recording device(s) 147, the audio recording device(s) 148, and the data storage 150 generally may be configured in a manner similar to that described above with respect to the corresponding components of the prescribing system 110. The indicator(s) 149 is configured to provide an indication (e.g., visual, audible, haptic, etc.) of one or more states of one or more components of the treatment system 140, as described below.

As shown in FIG. 1D, the data storage 150 stores one or more operating systems (O/S) 151, one or more database management systems (DBMS) 152, and one or more program module(s), applications, engines, computer-executable code, scripts, or the like, such as, for example, one or more communication module(s) 153, one or more stimulation module(s) 154, one or more subject verification module(s) 155, one or more stimulation parameter verification module(s) 156, one or more headpiece verification module(s) 157, one or more headpiece positioning verification module(s) 158, and one or more stimulation history generation module(s) 159. Some or all of these modules may be or include sub-modules. It should be appreciated that the program modules depicted in FIG. 1D as being stored in the data storage 150 are merely illustrative and not exhaustive and that the processing described as being supported by any particular module may alternatively be distributed across multiple modules or performed by a different module. Any of the components depicted as being stored in the data storage 150 may include any combination of software, firmware, and/or hardware. The software and/or firmware may include computer-executable code, instructions, or the like that may be loaded into the memory 142 for execution by one or more of the processor(s) 141. Any of the components depicted as being stored in data storage 150 may support the functionality described in reference to the corresponding components named herein. The O/S 151 may be loaded from the data storage 150 into the memory 142 and provide an interface between software executing on the treatment system 140 and the hardware resources of the treatment system 140. The DBMS 152 may be loaded into the memory 142 and support functionality for accessing, retrieving, storing, and/or manipulating data stored in the memory 142 and/or data stored in the data storage 150.

The communication module(s) 153 includes computer-executable instructions, code, or the like that, responsive to execution by one or more of the processor(s) 141 perform functions including, but not limited to, communicating with remote servers, communicating with remote datastores, communicating with other electronic devices, sending or receiving information and instructions, and the like. The stimulation module(s) 154 includes computer-executable instructions, code, or the like that, responsive to execution by one or more of the processor(s) 141 perform functions including, but not limited to, causing the stimulator(s) 145 to generate electric pulses, causing the magnetic coil(s) 146 to deliver magnetic stimulation to a subject, and the like.

The subject verification module(s) 145 includes computer-executable instructions, code, or the like that, responsive to execution by one or more of the processor(s) 141 perform functions including, but not limited to, receiving subject data, such as one or more subject identifiers associated with a subject, receiving stimulation parameter data, such as one or more parameters associated with operation of the stimulator(s) 145 or the magnetic coil(s) 146 for a subject, receiving security data, such as image data and/or audio data associated with a subject, determining an identity of a subject associated with subject data based at least in part on security data, determining whether a subject corresponds to stimulation parameter data based at least in part on the security data, and the like.

The stimulation parameter verification module(s) 156 includes computer-executable instructions, code, or the like that, responsive to execution by one or more of the processor(s) 141 perform functions including, but not limited to, receiving stimulation parameter data for a subject, determining whether stimulation parameter data is valid for a subject, determining whether stimulation parameter data should be updated for a subject, determining whether new stimulation parameter data for a subject supersedes a portion or all of existing stimulation parameter data for the subject, and the like.

The headpiece verification module(s) 157 includes computer-executable instructions, code, or the like that, responsive to execution by one or more of the processor(s) 141 perform functions including, but not limited to, receiving first, reference image data corresponding to one or more first, reference images of at least a portion of a subject and at least a portion of a headpiece 161 of the treatment system 140, receiving second image data from the image recording device(s) 147, the second image data corresponding to one or more second images of at least a portion of the subject and at least a portion of the headpiece 161, and determining whether the headpiece 161 corresponds to the subject (i.e., whether the subject is the intended subject associated with the headpiece 161) based at least in part on the first image data and the second image data, and the like.

The headpiece positioning verification module(s) 158 includes computer-executable instructions, code, or the like that, responsive to execution by one or more of the processor(s) 141 perform functions including, but not limited to, receiving first, reference image data corresponding to one or more first, reference images of at least a portion of a subject and at least a portion of the headpiece 161, receiving second image data from the image recording device(s) 147, the second image data corresponding to one or more second images of at least a portion of the subject and at least a portion of the headpiece 161, and determining whether the headpiece 161 is positioned at a pre-determined position relative to a target anatomy of the subject based at least in part on the first image data and the second image data, and the like.

Figure 1E:
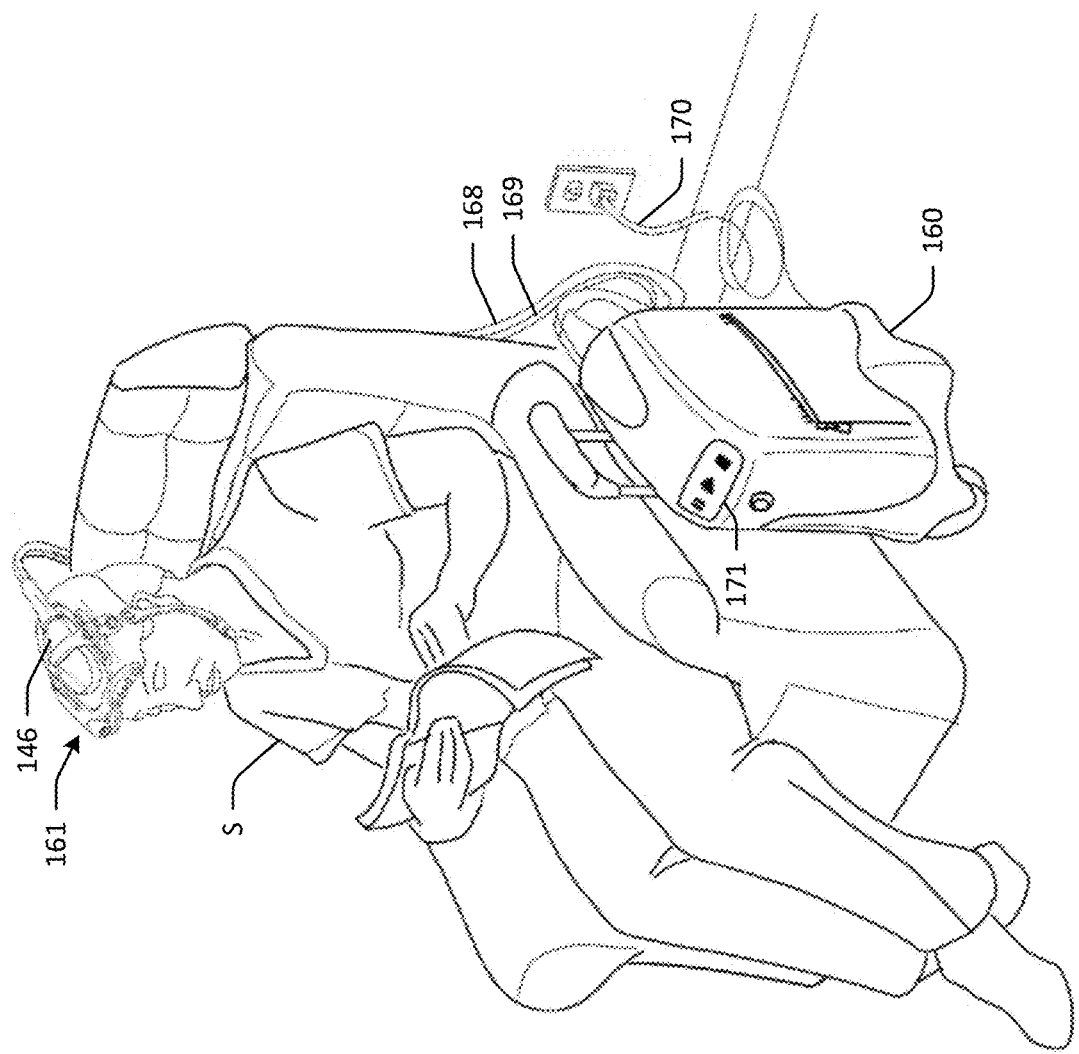
Figure 1E:
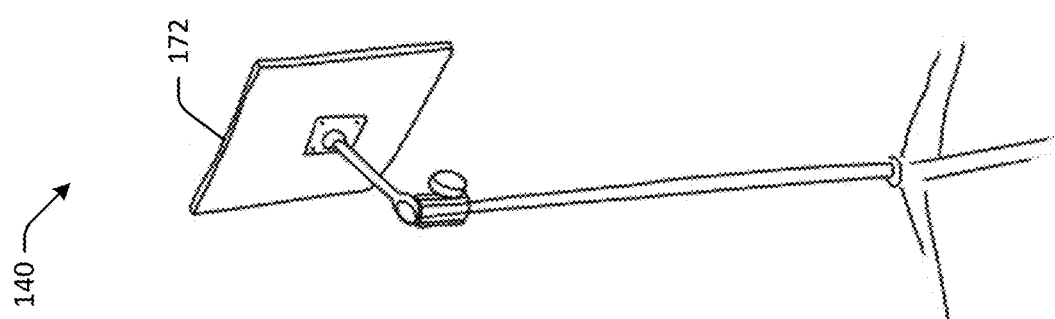
Figure 1F:
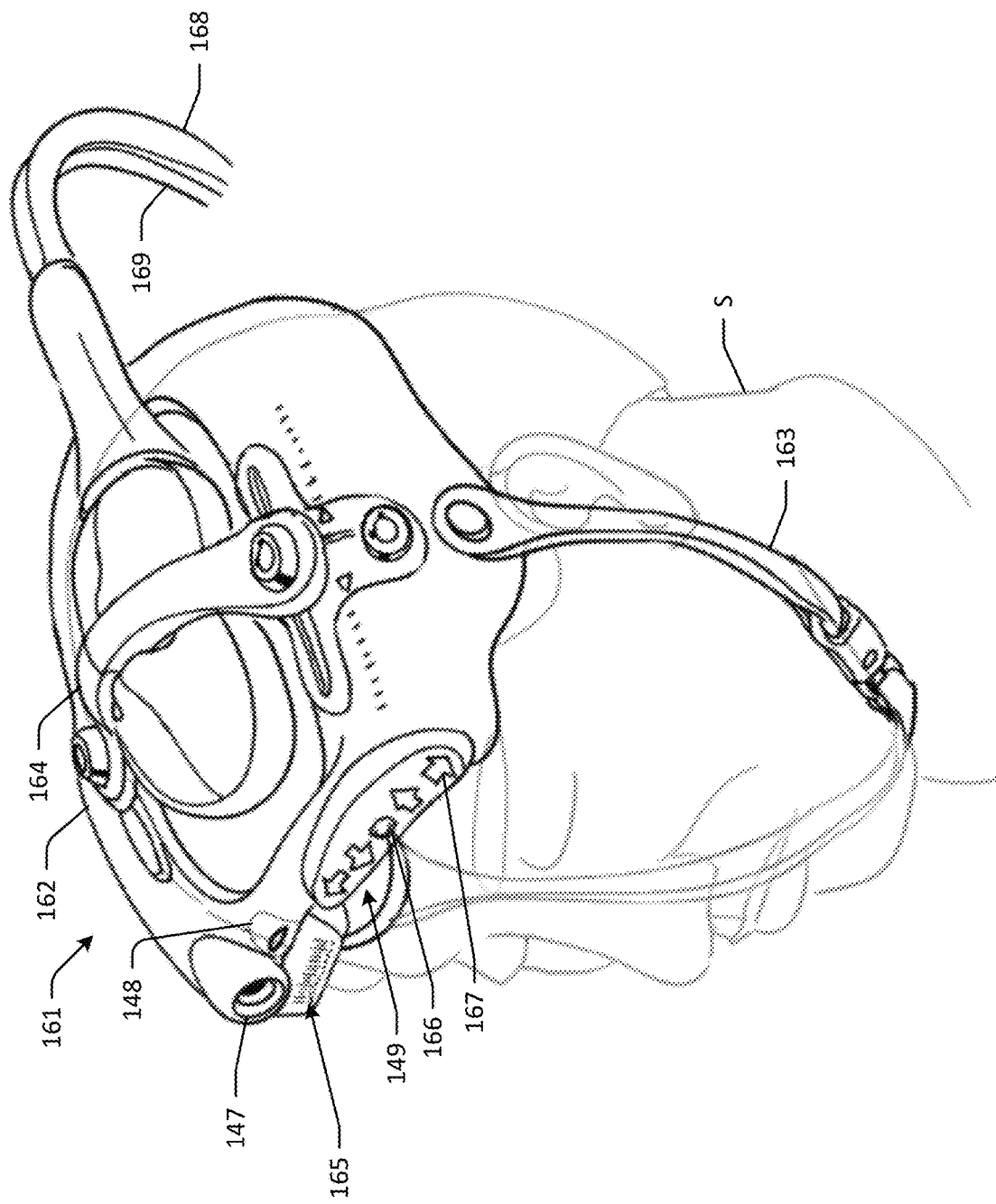

FIGS. 1E and 1F illustrate an example implementation of the treatment system 140. As shown, the treatment system 140 includes an electronics unit 160 and the headpiece 161 in communication with one another. The electronics unit 160 may include one or more of the processor(s) 141, the memory device(s) 142, the I/O interface(s) 143, the network interface(s) 144, the stimulator(s) 145, and the data storage 150 described above. For example, such components may be contained within a housing of the electronics unit 160 or mounted thereon.

As shown, the headpiece 161 includes the magnetic coil(s) 146, a body 162, a support mechanism 163, a secure locking means 164, and one or more headpiece identifier(s) 165. The headpiece 161 is configured to engage the head of the subject S and to be positioned at a pre-determined position relative to a target anatomy of the subject S. As noted above, the pre-determined position may be a parameter of the stimulation parameter data for the subject S. The body 162 is configured to be positioned about the head of the subject S such that the magnetic coil(s) 146 is properly positioned to stimulate the target anatomy. The body 162 may be formed as a helmet-like structure for positioning about the head of the subject S, as shown, although other shapes and configurations of the body 162 may be used. The body 162 also provides a structure for supporting the other components of the headpiece 161. In some embodiments, as shown, the image recording device(s) 147 and the audio recording device(s) 148 are mounted to the body 162. In other embodiments, the image recording device(s) 147 and the audio recording device(s) 148 may be separate from the headpiece 161. The support mechanism 163 is configured to secure the headpiece 161 relative to the head of the subject S, for example, to maintain the headpiece 161 in the pre-determined position. The secure locking means 164 is configured to mount the magnetic coil(s) 146 at a fixed location relative to the body 162. The fixed location of the magnetic coil(s) 146 relative to the body 162 corresponds to the pre-determined position of the headpiece 161 relative to the target anatomy of the subject S. In this manner, when the headpiece 161 is positioned at the pre-determined position, the magnetic coil(s) 146 is properly positioned to direct the magnetic field induced thereby to the target anatomy. In some embodiments, as shown, the secure locking means 164 may include a bracket and one or more fasteners, although other types of means for securely locking the magnetic coil(s) 146 at a fixed location may be used, such as one or more adhesives, glues, mechanical couplings, straps, clamps, and the like. The secure locking means 164 is configured such that the fixed location of the magnetic coil(s) 146 cannot be altered by unauthorized persons, including the subject S. The magnetic coil(s) 146 is mounted at the fixed location by authorized persons during initial setup of the headpiece 161 for the subject S, and the secure locking means 164 prevents movement of the magnetic coil(s) 146 relative to the body 162 after setup. For example, the secure locking means 164 may require a unique key or removal tool for unlocking and allowing movement of the magnetic coil(s) 146.

The headpiece identifier(s) 165 includes one or more identifiers associated with the headpiece 161 and configured to allow the headpiece 161 to be uniquely identified. For example, the headpiece identifier(s) 165 may include one or more of a barcode, a radio frequency identification (RFID) tag, a structural pattern, or other type of unique identifier. The headpiece identifier(s) 165 may include one or more encrypted identifiers. As described below, the headpiece identifier(s) 165 may be included in images captured by the image recording device(s) 147. In this manner, images including the headpiece identifier(s) 165 may be used to determine whether the headpiece 161 is associated with a person wearing the headpiece 161 (i.e., whether the person wearing the headpiece 161 is the intended subject S). Further, images including the headpiece identifier(s) 165 and the head of the subject S may be used to determine whether the headpiece 161 is properly positioned for treatment (i.e., whether the headpiece 161 is positioned at the pre-determined position relative to the head of the subject S). In some embodiments, one or more of the indicators 149 of the treatment system 140 are provided as a part of the headpiece 161. In the example of FIG. 1F, the headpiece 161 includes a first indicator 166 and a plurality of second indicators 167 mounted to the body 162. The first indicator 166 is configured to indicate that the headpiece 161 is at the pre-determined position, while the second indicators 167 are configured to indicate that the headpiece 161 is not at the pre-determined position and to indicate a desired movement of the headpiece 161 relative to the head of the subject S toward the pre-determined position. In some embodiments, the indicators 166, 167 may include lights, such as light-emitting diodes (LEDs), although other types of visual indicators may be used. In some embodiments, the headpiece 161 may include an electronic display, with the indicators 166, 167 being selectively presented at the electronic display. During positioning of the headpiece 161 on the head of the subject S, one or more of the second indicators 167 may be activated to indicate that headpiece 161 is not at the pre-determined position and to indicate a desired direction of movement (e.g., up, down, right, or left) of the headpiece 161 relative to the head of the subject S to reach the pre-determined position. Once the headpiece 161 is properly positioned, the first indicator 166 may be activated to inform the subject S that the headpiece 161 is at the pre-determined position. In some embodiments, the headpiece 161 may include non-visual indicators, such as audible or haptic indicators, instead of or in addition to visual indicators for indicating whether the headpiece 161 is at the pre-determined position and/or a desired movement of the headpiece 161 relative to the head of the subject S toward the pre-determined position.

As shown in FIG. 1E, the treatment system 140 also includes a mirror 172 configured to reflect light. During use of the treatment system 140, the mirror 172 is positioned in front of the subject S at a suitable distance such that a reflection of the face of the subject S and the headpiece 161 are visible to the subject S. In this manner, the subject S is able to view the reflection of the headpiece 161, including the indicators 166, 167 thereof, to self-position the headpiece 161 at the pre-determined position. As shown, the indicators 166, 167 may be positioned along the front of the body 162, such that the reflection of the indicators 166, 167 is visible to the subject S. The mirror 172, when properly positioned relative to the subject S, also allows the image recording device(s) 147 to capture images of the face of the subject S and the headpiece 161 reflected by the mirror 172. As shown, the image recording device(s) 147 may be positioned along the front of the body 162, such that a reflection of the headpiece 161 and the face of the subject S is visible to the image recording device(s) 147 when a reflection of the face of the subject S and the headpiece 161 is visible to the subject S. In this manner, the subject S is able to self-align the image recording device(s) 147 or the headpiece 161 with the mirror 172. As shown, the headpiece identifier(s) 165 also may be positioned along the front of the body 162, such that images of the headpiece 161 and the face of the subject S captured by the image recording device(s) 147 include the headpiece identifier(s) 165 for use in determining whether the headpiece 161 is associated with the subject S. It will be appreciated that the mirror 172 may be omitted in some embodiments of the treatment system 140, for example, when the image recording device(s) 147 and/or the indicators 166, 167 are not mounted to the body 162 of the headpiece 161.

In the example of FIG. 1E, the treatment system 140 also includes one or more power cable(s) 168 and one or more communication cable(s) 169 extending between the electronics unit 160 and the headpiece 161. The power cable(s) 168 provide power from the electronics unit 160 to the headpiece 161 for operating various components of the headpiece 161. The power cable(s) 168 also transmit the electric pulses generated by the stimulator(s) to the magnetic coil(s) 146. The communication cable(s) 169 provide communication between the electronics unit 160 and the headpiece 161, including the exchange of control signals during operation of the treatment system 140. As shown, the treatment system 140 also includes a network cable 170 extending from the electronics unit 170 and configured to facilitate communication between the treatment system 140 and the network(s) 102. It will be appreciated that, in other embodiments, wireless means of communication between the headpiece 161, the electronics unit 160, and/or the network(s) 102 may be used.

During use of the treatment system 140, the subject S may control operation of the treatment system 140 via a user interface 171. In some embodiments, as shown, the user interface 171 may be provided as a part of the electronics unit 160, although other configurations may be used. The user interface 171 may include a plurality of selectable elements, such as buttons, switches, and the like, for selection by the subject S. For example, the user interface 171 may include a power button, a start button, a stop button, a pause button, and the like to control magnetic stimulation provided by the treatment system 140 during a treatment session. The subject S also may control operation of the treatment system 140 via the audio recording device(s) 148. For example, the audio recording device(s) 148 may capture an audio recording of the subject S including a verbal command (e.g., start, stop, pause, etc.). In some embodiments, the treatment system 140 may respond only to verbal commands by the intended subject S and not verbal commands by other persons. For example, the treatment system 140 may use a first, reference audio recording for the subject S to determine whether a second audio recording captured by the audio recording device(s) 148 is associated with the subject S. Although the treatment system 140 is configured to allow the subject S to control operation of the treatment system 140 during a treatment session, the treatment system 140 alternatively may be operated by an assistant who, like the subject S, has only minimal clinical training.

To enable point-of-care magnetic stimulation therapy, the magnetic stimulation system 100 may execute one or more process flows. An example process flow 180 for managing and performing magnetic stimulation to treat a patient is depicted in FIG. 1A.

At block 181 of the process flow 180, the prescribing system 110 may determine stimulation parameter data for a subject. The stimulation parameter data may be determined based at least in part on one or more indications of user input provided by a trained clinician operating the prescribing system 110. The stimulation parameter data may include a plurality of parameters associated with operation of the stimulator 115 or the magnetic coil 116 for the subject. For example, the parameters may include a magnitude and a timing sequence of electric pulses generated by the stimulator 115, a magnitude of magnetic stimulation delivered by the magnetic coil 116, a position of the magnetic coil 116 relative to a target anatomy of the subject, and other parameters defining a treatment protocol for treating the subject's disorder (i.e., the subject's magnetic stimulation prescription). Use of the prescribing system 110 may begin with determining the subject's motor threshold level and motor threshold location in a conventional manner. The clinician may interact with the user interface 132 to cause the stimulator 115 to generate magnetic pulses and to cause the magnetic coil 116 to deliver magnetic stimulation to the subject's brain. The clinician may move the magnetic coil 116 over the subject's head to isolate a particular muscle location in the subject's brain and may vary the power level of magnetic stimulation to determine the subject's motor threshold level and motor threshold location. The clinician then may determine the subject's treatment power level based on the subject's motor threshold level. A target anatomy of the subject's brain may be determined based on the disorder to be treated (e.g., using one or more algorithms corresponding to relationships between particular disorders and areas of the human brain known to be underactive or overactive for such disorders), and a desired position of the magnetic coil 116 relative to the target anatomy may be determined for directing magnetic stimulation at the target anatomy. The prescribing system 110 also may determine subject data for the subject. The subject data may include one or more subject identifiers associated with the subject. The subject identifiers may include, for example, a name of the subject, an identification number for the subject, or other information that may be used alone or in combination to uniquely identify the subject. In some instances, the prescribing system 110 may determine the subject data based on one or more indications of user input received from the user interface 132. The prescribing system 110 may cause the subject data and the stimulation parameter data to be stored in association with one another. In this manner, the association between the subject data and the stimulation parameter data may be used by the magnetic stimulation system 100 to ensure that treatment of the subject is administered in accordance with the stimulation parameter data for the subject. The subject data and the stimulation parameter data may be stored locally at the prescribing system 110. The subject data and the stimulation parameter data also may be provided to and stored at the data server 104 and/or the treatment system 140. The subject data and the stimulation parameter data may be stored and transmitted in an encrypted format to inhibit unauthorized access to the raw data.

In some embodiments, the prescribing system 110 may be used to generate or otherwise determine security data for the subject. The security data may include image data, audio data, and/or other types of data that may be used by the magnetic stimulation system 100 to determine or verify an identity of a subject. For example, the image recording device 117 of the prescribing system 110 may be used to capture one or more images of the subject and generate image data corresponding to the one or more images. Additionally or alternatively, the audio recording device 118 of the prescribing system 110 may be used to capture one or more audio recordings of the subject and generate audio data corresponding to the one or more audio recordings. In some embodiments, the prescribing system 110 may include other devices for generating other types of security data, such as retinal signature data or fingerprint data, which may be used for determining or verifying an identity of a subject. In some embodiments, the security data may be generated by another system separate from the prescribing system 110 and provided to the prescribing system 110, the data server 104, and/or the treatment system 140. In some embodiments, the security data may be generated by the treatment system 140 during initial setup and customization of the treatment system 140 for the subject and then provided to the prescribing system 110 and/or the data server 104. As described herein, the security data may be used by the treatment system 140 to determine whether the stimulation parameter data for the treatment system 140 is associated with a subject attempting to use the treatment system 140 (i.e., whether a subject is the intended subject for the treatment system 140), whether the headpiece 161 is associated with a subject attempting to use the headpiece 161 (i.e., whether a subject is the intended subject for the headpiece 161), and/or whether a verbal command received by the treatment system 140 is associated with a subject (i.e., whether a verbal command was made by the intended subject or another person).

After the stimulation parameter data for the subject has been determined using the prescribing system 110, the treatment system 140 may be setup and customized for the subject. Such setup and customization of the treatment system 140 may be performed at an equipment dispensary, which may be at the same clinical location as the prescribing system 110 or a different location. The headpiece 161 of the treatment system 140 may be configured for the intended subject. For example, the magnetic coil 146 may be positioned relative to the body 162 of the headpiece 161, and the secure locking means 164 may be used to mount the magnetic coil 146 at a fixed location relative to the body 162, with the fixed location corresponding to a pre-determined position of the headpiece 161 relative to the target anatomy of the subject. In this manner, when the headpiece 161 is at the pre-determined position relative to the target anatomy, the magnetic coil 146 is properly positioned to stimulate the target anatomy. Customization of the headpiece 161 for the subject also may include forming or affixing the headpiece identifier 165, with the headpiece identifier 165 being associated with the headpiece 161 and the subject.

At block 182 of the process flow 180, the treatment system 140 may receive the stimulation parameter data and first image data for the subject. In some embodiments, the stimulation parameter data and the first image data may be received by and stored at the treatment system 140 during setup and customization of the treatment system 140 for the subject. The subject data also may be received by and stored at the treatment system 140 in association with the stimulation parameter data and the first image data during setup of the treatment system 140. The first image data may correspond to one or more first images of at least a portion of the subject and at least a portion of the headpiece 161. For example, the one or more first images may include at least a portion of the subject's face and at least a front portion of the headpiece 161 including the headpiece identifier 165. The one or more first images may be captured while the headpiece 161 is at the pre-determined position relative to the target anatomy of the subject. In some embodiments, the one or more first images may be captured by the image recording device 147 of the treatment system 140. In some embodiments, the one or more first images may be captured by the image recording device 117 of the prescribing system 110, and the first image data may be provided to the treatment system 140. In some embodiments, the one or more first images may be captured by a system other than the prescribing system 110 and the treatment system 140, and the first image data may be provided to the treatment system 140. In some embodiments, the first image data also may be provided to and stored at the data server 104. As described herein, the first image data may be used by the treatment system 140 to determine whether the headpiece 161 is associated with a subject attempting to use the headpiece 161 (i.e., whether a subject is the intended subject for the headpiece 161), and/or whether the headpiece 161 is properly positioned on the head of the subject (i.e., whether the headpiece 161 is at the pre-determined position relative to the target anatomy of the subject). In this manner, the first image data may be used by the treatment system 140 as reference data for making such determinations. After the treatment system 140 has been configured for the subject, the subject may transport the treatment system 140 to a remote location relative to the prescribing system 110 for use. For example, the treatment system 140 may be taken to the subject's home or other location for convenient point-of-care use.

At block 183 of the process flow 180, the treatment system 140 may receive second image data for the subject. The second image data may correspond to one or more second images of at least a portion of the subject and at least a portion of the headpiece 161. The one or more second images may be captured prior to beginning a magnetic stimulation treatment session. The one or more second images may be captured by the image recording device 147 of the treatment system 140. As described above, during use of the treatment system 140, the subject may position the headpiece 161 on the subject's head while the subject is seated in a chair and faces the mirror 172, and the image recording device 147 may capture the one or more second images using the mirror 172. The one or more second images may include at least a portion of the subject's face and at least a front portion of the headpiece 161 including the headpiece identifier 165. As described herein, the second image data may be used by the treatment system 140 to determine whether the stimulation parameter data for the treatment system 140 is associated with a subject attempting to use the treatment system 140 (i.e., whether a subject is the intended subject for the treatment system 140), whether the headpiece 161 is associated with a subject attempting to use the headpiece 161 (i.e., whether a subject is the intended subject for the headpiece 161), and/or whether the headpiece 161 is properly positioned on the head of the subject (i.e., whether the headpiece 161 is at the pre-determined position relative to the target anatomy of the subject). In some embodiments, the second image data also may be provided to and stored at the data server 104 and/or the prescribing system 110.

At block 184 of the process flow 180, the treatment system 140 may use the first image data and the second image data to determine that the stimulation parameter data corresponds to the subject. In some embodiments, the treatment system 140 may compare the first image data and the second image data to determine that the stimulation parameter data corresponds to the subject. For example, the treatment system 140 may use one or more facial recognition algorithms to compare the first image data and the second image data and determine whether the subject is the intended subject associated with the stimulation parameter data. In some embodiments, one or more facial recognition algorithms may use the one or more first images to determine one or more facial characteristics of the intended subject and then may determine whether the one or more facial characteristics are present in the one or more second images. Various approaches may be used for analyzing the first image data and the second image data to determine whether the stimulation parameter data corresponds to the subject. In some embodiments, the treatment system 140 may enable operation of the stimulator 145 and/or the magnetic coil 146 based at least in part on the determination that the stimulation parameter data corresponds to the subject.

At block 185 of the process flow 180, the treatment system 140 may use the second image data to determine that the headpiece 161 corresponds to the subject. In some embodiments, the treatment system 140 may use the headpiece identifier 165 and the face of the subject in the one or more second images to determine that the headpiece 161 corresponds to the subject. In some embodiments, the treatment system 140 may use one or more object and facial recognition algorithms to determine whether the subject is the intended subject associated with the headpiece 161. Various approaches may be used for analyzing the second image data to determine whether the headpiece 161 corresponds to the subject. In some embodiments, the treatment system 140 may enable operation of the stimulator 145 and/or the magnetic coil 146 based at least in part on the determination that the headpiece 161 corresponds to the subject.

In some embodiments, the treatment system 140 may use the first image data and the second image data to determine whether the headpiece 161 is properly positioned on the head of the subject (i.e., whether the headpiece 161 is at the pre-determined position relative to the target anatomy of the subject). In some embodiments, the treatment system 140 may compare the first image data and the second image data to determine whether the headpiece 161 is at the pre-determined position. For example, the treatment system 140 may use one or more object and facial recognition algorithms to compare the first image data and the second image data and determine whether the headpiece 161 is at the pre-determined position. In some embodiments, one or more object and facial recognition algorithms may use the one or more first images to determine a position of the headpiece 161 relative to one or more facial features of the subject in the one or more first images and then may determine whether the headpiece 161 is similarly positioned relative to the one or more facial features of the subject in the one or more second images. Various approaches may be used for analyzing the first image data and the second image data to determine whether the headpiece 161 is at the pre-determined position. In some embodiments, the treatment system 140 may enable operation of the stimulator 145 and/or the magnetic coil 146 based at least in part on the determination that the headpiece 161 is at the pre-determined position. As described above, the treatment system 140 may cause the first indicator 166 to be activated based at least in part on the determination that the headpiece 161 is at the pre-determined position, thereby informing the subject that the headpiece 161 is at the pre-determined position. In some embodiments, the treatment system 140 may determine that the headpiece 161 is not at the pre-determined position. As described above, the treatment system 140 may cause one or more of the second indicators 167 to be activated based at least in part on the determination that the headpiece 161 is not at the pre-determined position, thereby informing the subject that the headpiece 161 is not at the pre-determined position and indicating a desired direction of movement (e.g., up, down, right, or left) of the headpiece 161 relative to the head of the subject to reach the pre-determined position.

In some embodiments, the treatment system 140 may determine whether the headpiece 161 is at the pre-determined position prior to beginning a treatment session and may monitor positioning of the headpiece 161 throughout the treatment session (i.e., while magnetic stimulation is being administered to the subject). In other words, the treatment system 140 may ensure that the headpiece 161 remains at the pre-determined position throughout the treatment session. For example, the treatment system 140 may periodically receive additional image data corresponding to one or more additional images of at least a portion of the subject and at least a portion of the headpiece 161 captured by the image recording device 147 during the treatment session. In some embodiments, the treatment system 140 may use the first image data and the additional image data to determine that the headpiece 161 is not at the pre-determined position during the treatment session (i.e., the headpiece 161 has moved away from the pre-determined position during the treatment session). In such instances, the treatment system 140 may cause operation of the stimulator 145 and/or the magnetic coil 146 to be paused or stopped based at least in part on the determination that the headpiece 161 is not at the pre-determined position. Further, the treatment system 140 may cause one or more of the second indicators 167 to be activated based at least in part on the determination that the headpiece 161 is not at the pre-determined position, thereby informing the subject that the headpiece 161 is not at the pre-determined position and indicating a desired direction of movement (e.g., up, down, right, or left) of the headpiece 161 relative to the head of the subject to reach the pre-determined position. The treatment system 140 may cause operation of the stimulator 145 and/or the magnetic coil 146 to be resumed based at least in part on a subsequent determination that the headpiece 161 is at the pre-determined position.

In some embodiments, the treatment system 140 may monitor a state of the subject (e.g., awake state, asleep state, seizure state, etc.) throughout a treatment session (i.e., while magnetic stimulation is being administered to the subject). In other words, the treatment system 140 may ensure that the subject remains in a desired state (e.g., awake state) throughout the treatment session and may respond accordingly in the event of onset of an undesired state (e.g., asleep state, seizure state, etc.) during the treatment session. For example, the treatment system 140 may periodically receive additional image data corresponding to one or more additional images of at least a portion of the subject captured by the image recording device 147 during the treatment session. In some embodiments, the additional image data may be the same image data used by the treatment system 140 for determining whether the headpiece 161 is at the pre-determined position during the treatment session. The treatment system 140 may use one or more facial recognition algorithms to determine a state of the subject based at least in part on the additional image data. Various approaches may be used for analyzing the additional image data to determine the state of the subject.

In some embodiments, the treatment system 140 may determine that the additional image data is indicative of an awake state (i.e., the subject is awake). In such instances, the treatment system 140 may cause operation of the stimulator 145 and the magnetic coil 146 to be maintained based at least in part on the determination that the state of the subject is the awake state. In some embodiments, the treatment system 140 may determine that the additional image data is indicative of an asleep state (i.e., the subject is asleep or falling asleep). In such instances, the treatment system 140 may cause operation of the stimulator 145 and/or the magnetic coil 146 to be paused or stopped based at least in part on the determination that the state of the subject is the asleep state. Further, the treatment system 140 may cause one or more alarms, such as visual, audible, or haptic alarms, of the treatment system 140 to be activated based at least in part on the determination that the state of the subject is the asleep state, thereby urging the subject to wake up. The treatment system 140 may cause operation of the stimulator 145 and/or the magnetic coil 146 to be resumed based at least in part on a subsequent determination that the state of the subject is the awake state. In some embodiments, the treatment system 140 may determine that the additional image data is indicative of a seizure state (i.e., the subject is experiencing a seizure). In such instances, the treatment system 140 may cause operation of the stimulator 145 and/or the magnetic coil 146 to be disabled or stopped based at least in part on the determination that the state of the subject is the seizure state. Further, the treatment system 140 may cause an emergency message indicative of the seizure state to be sent to the prescribing system 110, the supervising clinician user device 106, and/or the emergency response user device 108.

In some embodiments, the treatment system 140 may enable operation of the stimulator 145 and/or the magnetic coil 146 based at least in part on a determination that one or more stimulation conditions are met. For example, the treatment system 140 may enable operation of the stimulator 145 and/or the magnetic coil 146 based at least in part on a determination that one or more (in any combination), or all, of the following stimulation conditions are met: (i) the stimulation parameter data is associated with the subject; (ii) the headpiece 161 is associated with subject; (iii) the headpiece 161 is at the pre-determined position; and (iv) the state of the subject is the awake state.

In some embodiments, the treatment system 140 may change an operational state (e.g., off, on, paused, etc.) of the stimulator 145 based at least in part on one or more indications of interaction by the subject (or an assistant aiding the subject) with the user interface 171. The treatment system 140 may receive an indication of interaction by the subject with the user interface 171, with the indication of interaction being associated with an operational state that is different from a current operational state of the of the stimulator 145. For example, the treatment system 140 may cause the stimulator 145 to assume a first operational state (e.g., on state) and may subsequently receive an indication of interaction that is associated with a different second operational state (e.g., off state). In such instances, the treatment system 140 may cause the stimulator 145 to assume the second operational state based at least in part on the indication of interaction.

In some embodiments, the treatment system 140 may change an operational state (e.g., off, on, paused, etc.) of the stimulator 145 based at least in part on an audio recording of the subject that includes a verbal command (e.g., start, stop, pause, etc.). The treatment system 140 may receive audio data corresponding to one or more audio recordings of the subject, with the one or more audio recordings being indicative of a command associated with an operational state that is different from a current operational state of the of the stimulator 145. For example, the treatment system 140 may cause the stimulator 145 to assume a first operational state (e.g., on state) and may subsequently receive audio data corresponding to one or more audio recordings of the subject captured by the audio recording device 148, with the one or more audio recordings being indicative of a command associated with a different second operational state (e.g., off state). In such instances, the treatment system 140 may determine whether the received audio data is associated with the subject (i.e., whether the audio recording is of the intended subject). For example, the treatment system 140 may compare the received audio data with reference audio data for the subject to determine whether the received audio data is associated with the subject. In some embodiments, the treatment system 140 may determine that the received audio data is associated with the subject and may cause the stimulator 145 to assume the second operational state based at least in part on the determination that the received audio data is associated with the subject. In some embodiments, the treatment system 140 may determine that the received audio data is not associated with the subject (i.e., the audio recording is of a person other than the intended subject) and may cause the stimulator 145 to maintain the first operational state based at least in part on the determination that the received audio data is not associated with the subject. In this manner, the treatment system 140 may respond only to verbal commands by the intended subject and not verbal commands by other persons.

During a magnetic stimulation treatment session, the treatment system 140 may cause the stimulator 145 to generate a plurality of electric pulses and may cause the magnetic coil 146 to deliver magnetic stimulation to the subject. The treatment system 140 may cause the stimulator 145 to generate the plurality of electric pulses in accordance with the stimulation parameter data and may cause the magnetic coil 146 to deliver the magnetic stimulation to the subject in accordance with the stimulation parameter data. In some embodiments, the magnetic stimulation may be transcutaneous magnetic stimulation. In some embodiments, the magnetic stimulation may be transcranial magnetic stimulation. In some embodiments, the magnetic stimulation may be repetitive transcranial magnetic stimulation.

In some embodiments, the treatment system 140 may generate stimulation history data including one or more metrics associated with one or more stimulation sessions administered to the subject. For example, the treatment system 140 may generate stimulation history data after completion, or partial completion, of a stimulation session. In some embodiments, the treatment system 140 may send the stimulation history data, or otherwise cause the stimulation history data to be sent, to the prescribing system 110, the data server 104, and/or the supervising clinician user device 106. In this manner, the stimulation history data may be reviewed by the supervising clinician or other authorized persons to determine whether any modifications to the stimulation parameter data for the subject should be made. In some embodiments, the stimulation history data may be transmitted in an encrypted format to inhibit unauthorized persons from accessing the raw data.

In some embodiments, the treatment system 140 may receive new stimulation parameter data that is different, at least in part, from the initial stimulation parameter data received by the treatment system 140. In other words, the treatment system 140 may receive modifications or updates to the stimulation parameter data for the subject. In some embodiments, the treatment system 140 may receive new stimulation parameter data from the supervising clinician user device 106. For example, treatment system 140 may receive new stimulation parameter data from the supervising clinician user device 106 after sending stimulation history data or a request for updated stimulation parameter data to the supervising clinician user device 106. In some embodiments, the treatment system 140 may receive new stimulation parameter data from the prescribing system 110. For example, treatment system 140 may receive new stimulation parameter data from the prescribing system 110 after sending stimulation history data or a request for updated stimulation parameter data to the prescribing system 110. In some embodiments, the treatment system 140 may receive new stimulation parameter data from the data server 104. For example, treatment system 140 may receive new stimulation parameter data from the data server 104 after sending stimulation history data or a request for updated stimulation parameter data to the data server 104. In some embodiments, the new stimulation parameter data may be transmitted in an encrypted format to inhibit unauthorized persons from accessing the raw data. The treatment system 140 may determine that the new stimulation parameter data supersedes at least a portion of the initial stimulation parameter data, for example by comparing respective timestamps or status indicators associated with the new stimulation parameter data and the initial stimulation parameter data. In some embodiments, the treatment system 140 may cause the new stimulation parameter data to be stored locally at the treatment system 140 in association with the subject data and the first image data.

The treatment system 140 may be used to carry out a number of magnetic stimulation treatment sessions required by the treatment protocol for the subject. It will be appreciated that, in some embodiments, the operations described above with respect to blocks 181 and 182 of the process flow 180 may be carried out once for the subject, while the operations described above with respect to blocks 183, 184, and 185 of the process flow 180 may be carried out for each treatment sessions. After completion of the treatment protocol, the treatment system 140 may be turned in by the subject and reconfigured for use by a different subject.

Figure 2:
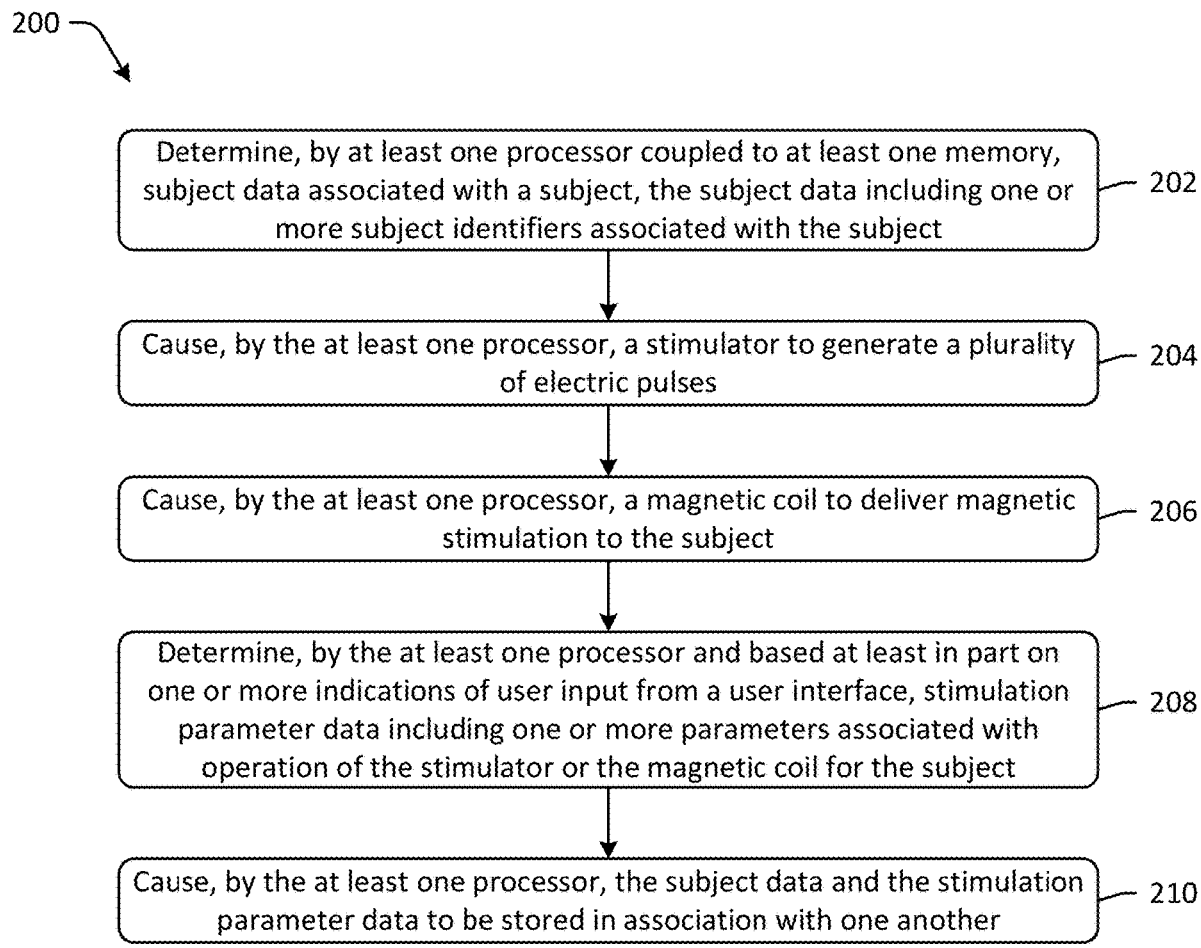
FIG. 2 illustrates an example process flow diagram for determining a magnetic stimulation prescription for a subject in accordance with one or more embodiments of the disclosure.

Referring to FIG. 2, an example process flow 200 for determining stimulation parameter data for a subject is depicted. Although certain operations are illustrated as occurring separately in FIG. 2, some or all of the operations may occur concurrently or partially concurrently. The operations of the process flow 200 may be executed by the prescribing system described above.

At block 202 of the process flow 200, subject data associated with a subject is determined, the subject data including one or more subject identifiers associated with the subject. For example, computer-executable instructions of the subject data determination module stored at the prescribing system may be executed to determine subject data associated with a subject.

At block 204 of the process flow 200, a stimulator is caused to generate a plurality of electric pulses. For example, computer-executable instructions of the stimulation module stored at the prescribing system may be executed to cause the stimulator to generate a plurality of electric pulses.

At block 206 of the process flow 200, a magnetic coil is caused to deliver magnetic stimulation to the subject. For example, computer-executable instructions of the stimulation module stored at the prescribing system may be executed to cause the magnetic coil to deliver magnetic stimulation to the subject.

At block 208 of the process flow 200, stimulation parameter data is determined based at least in part on one or more user inputs from a user interface, the stimulation parameter data including one or more parameters associated with operation of the stimulator or the magnetic coil for the subject. For example, computer-executable instructions of the stimulation parameter data determination module stored at the prescribing system may be executed to determine stimulation parameter data for the subject.

At block 210 of the process flow 200, the subject data and the stimulation parameter data are caused to be stored in association with one another. For example, computer-executable instructions of the stimulation parameter data determination module stored at the prescribing system may be executed to cause the subject data and the stimulation parameter data to be stored in association with one another.

Figure 3:
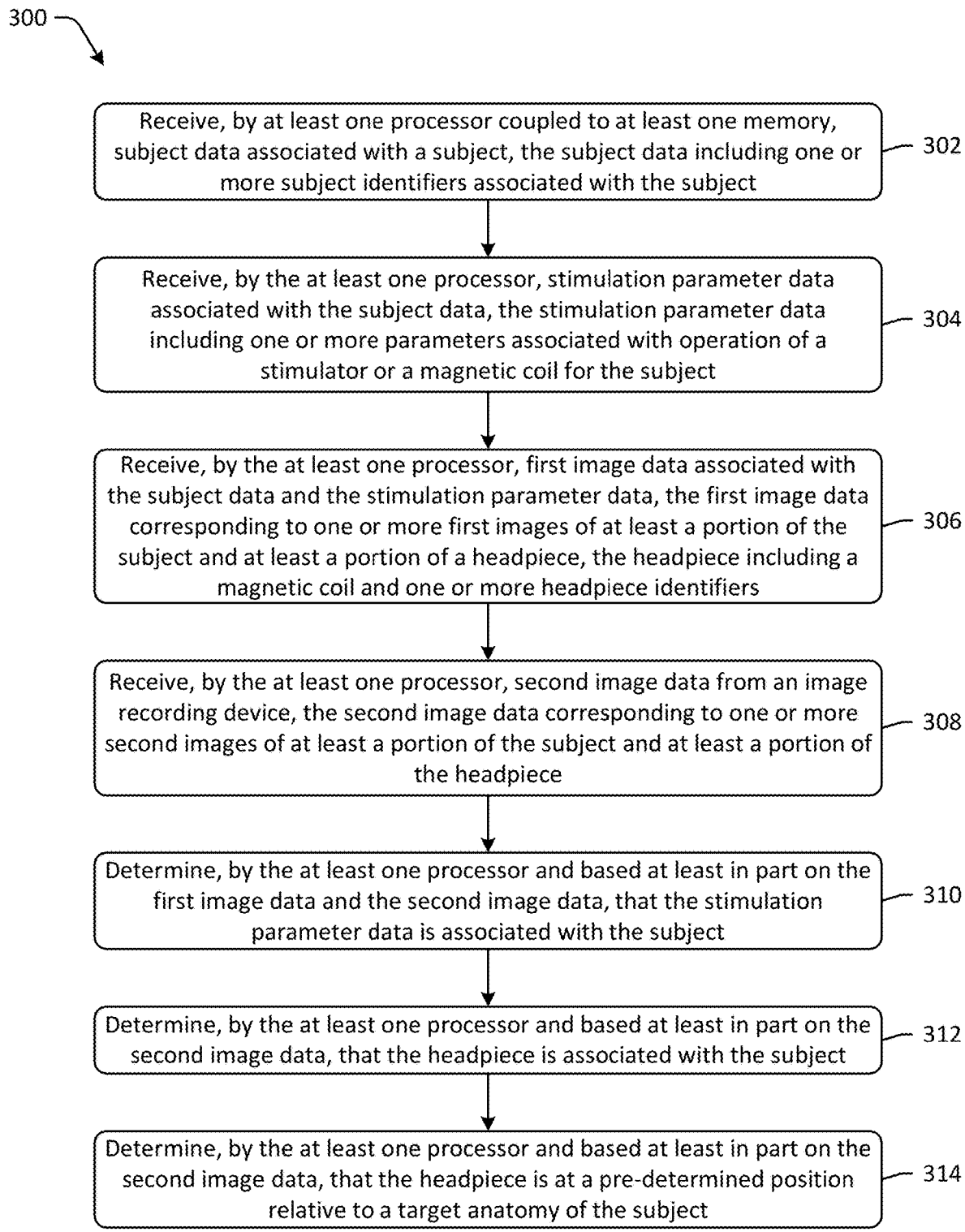
FIG. 3 illustrates an example process flow diagram for administering magnetic stimulation to a subject in accordance with one or more embodiments of the disclosure.

Referring to FIG. 3, an example process flow 300 for administering magnetic stimulation to a subject is depicted. Although certain operations are illustrated as occurring separately in FIG. 3, some or all of the operations may occur concurrently or partially concurrently. The operations of the process flow 300 may be executed by the treatment system described above.

At block 302 of the process flow 300, subject data associated with a subject is received, the subject data including one or more subject identifiers associated with the subject. For example, computer-executable instructions of the subject verification module stored at the treatment system may be executed to receive subject data associated with a subject.

At block 304 of the process flow 300, stimulation parameter data associated with the subject data is received, the stimulation parameter data including one or more parameters associated with operation of a stimulator or a magnetic coil for the subject. For example, computer-executable instructions of the subject verification module stored at the treatment system may be executed to receive stimulation parameter data associated with the subject data.

At block 306 of the process flow 300, first image data associated with the subject data and the stimulation parameter data is received, the first image data corresponding to a first image of at least a portion of the subject and at least a portion of a headpiece. For example, computer-executable instructions of the subject verification module stored at the treatment system may be executed to receive first image data associated with the subject data and the stimulation parameter data. The headpiece includes one or more headpiece identifiers associated with the headpiece, and a magnetic coil in communication with the stimulator and configured to deliver magnetic stimulation to the subject. The second magnetic coil being is mounted to a body of the headpiece at a fixed location by a secure locking means.

At block 308 of the process flow 300, second image data is received from an image recording device, the second image data corresponding to a second image of at least a portion of the subject and at least a portion of the headpiece. For example, computer-executable instructions of the subject verification module stored at the treatment system may be executed to receive second image data from an image recording device.

At block 310 of the process flow 300, it is determined, based at least in part on the first image data and the second image data, that the stimulation parameter data is associated with the subject. For example, computer-executable instructions of the subject verification module stored at the treatment system may be executed to determine, based at least in part on the first image data and the second image data, that the stimulation parameter data is associated with the subject.

At block 312 of the process flow 300, it is determined, based at least in part on the second image data, that the headpiece is associated with the subject. For example, computer-executable instructions of the headpiece verification module stored at the treatment system may be executed to determine, based at least in part on the second image data, that the headpiece is associated with the subject.

At block 314 of the process flow 300, it is determined, based at least in part on the second image data, that the headpiece is at a pre-determined position relative to a target anatomy of the subject. For example, computer-executable instructions of the headpiece positioning verification module stored at the treatment system may be executed to determine, based at least in part on the second image data, that the headpiece is at a pre-determined position relative to a target anatomy of the subject.

Figure 4A:
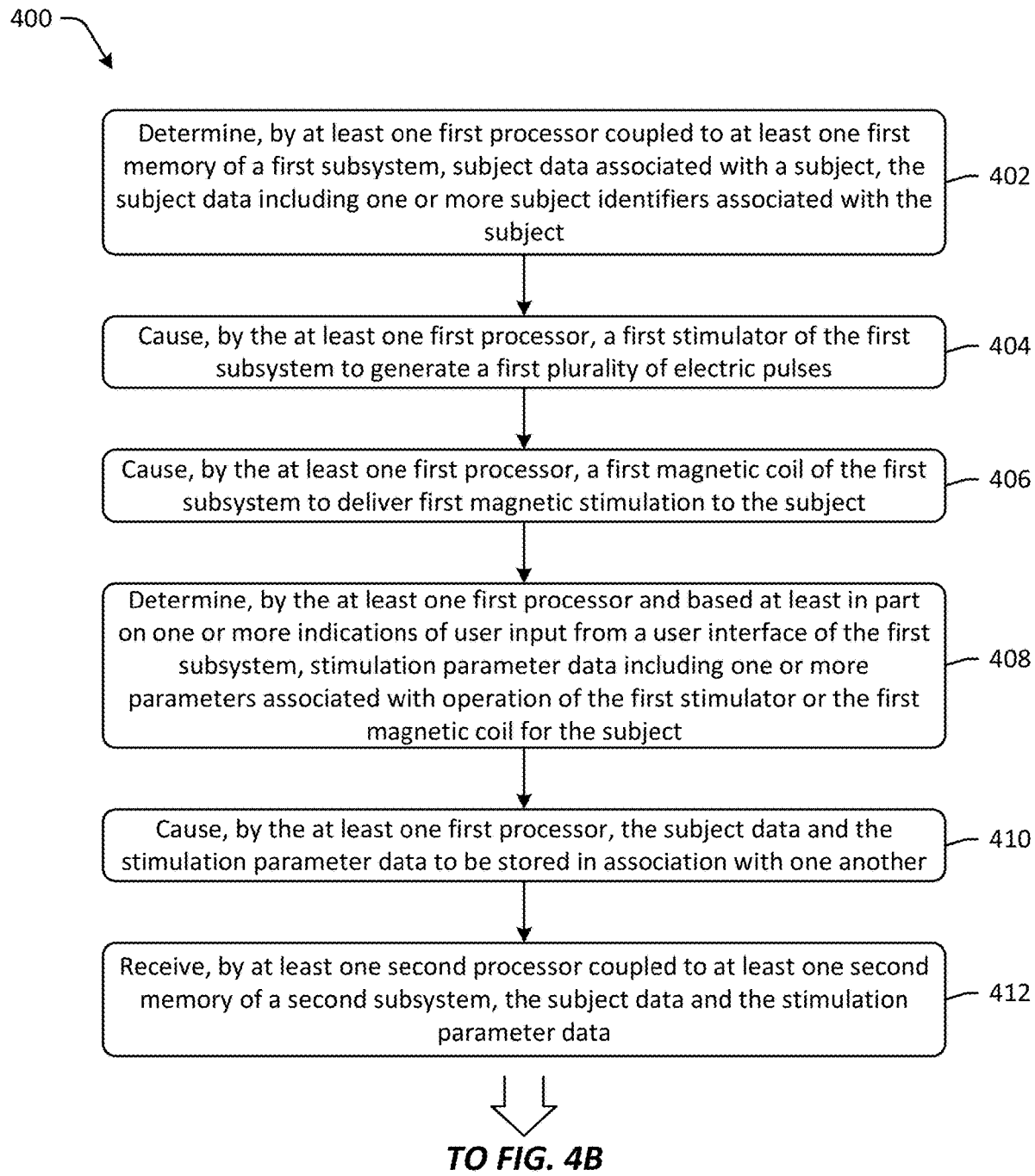
FIGS. 4A-4B illustrate an example process flow diagram for determining a magnetic stimulation prescription for a subject and administering magnetic stimulation to the subject in accordance with one or more embodiments of the disclosure.
Figure 4B:
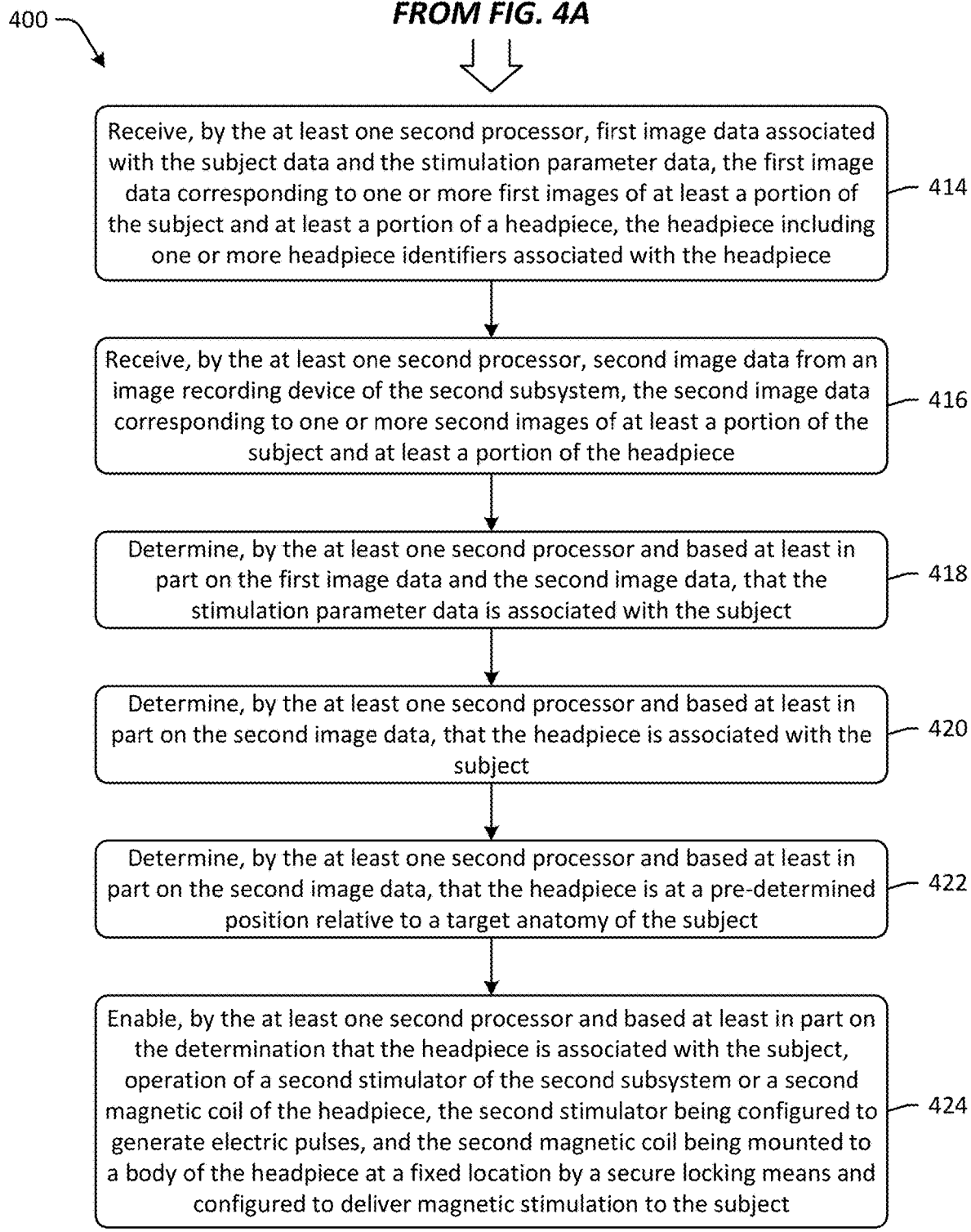

Referring to FIGS. 4A-4B, an example process flow 400 for determining stimulation parameter data for a subject and administering magnetic stimulation to the subject is depicted. Although certain operations are illustrated as occurring separately in FIG. 4, some or all of the operations may occur concurrently or partially concurrently. The operations of the process flow 400 may be executed by the magnetic stimulation system described above.

At block 402 of the process flow 400, subject data associated with a subject is determined by a first subsystem, the subject data including one or more subject identifiers associated with the subject. For example, computer-executable instructions of the first subsystem may be executed to determine subject data associated with a subject.

At block 404 of the process flow 400, a first stimulator of the first subsystem is caused to generate a plurality of first electric pulses. For example, computer-executable instructions of the first subsystem may be executed to cause the first stimulator to generate a plurality of first electric pulses.

At block 406 of the process flow 400, a first magnetic coil of the first subsystem is caused to deliver first magnetic stimulation to the subject. For example, computer-executable instructions of the first subsystem may be executed to cause the first magnetic coil to deliver first magnetic stimulation to the subject.

At block 408 of the process flow 400, stimulation parameter data is determined based at least in part on one or more user inputs from a user interface of the first subsystem, the stimulation parameter data including one or more parameters associated with operation of the first stimulator or the first magnetic coil for the subject. For example, computer-executable instructions of the first subsystem may be executed to determine stimulation parameter data based at least in part on one or more user inputs from a user interface of the first subsystem.

At block 410 of the process flow 400, the subject data and the stimulation parameter data are caused to be stored in association with one another. For example, computer-executable instructions of the first subsystem may be executed to cause the subject data and the stimulation parameter data to be stored in association with one another.

At block 412 of the process flow 400, the subject data and the stimulation parameter data are received by the second subsystem. For example, computer-executable instructions of the second subsystem may be executed to receive the subject data and the stimulation parameter data.

At block 414 of the process flow 400, first image data associated with the subject data and the stimulation parameter data is received by the second subsystem, the first image data corresponding to a first image of at least a portion of the subject and at least a portion of a headpiece. For example, computer-executable instructions of the second subsystem may be executed to receive first image data associated with the subject data and the stimulation parameter data. The headpiece includes one or more headpiece identifiers associated with the headpiece.

At block 416 of the process flow 400, second image data is received from an image recording device of the second subsystem, the second image data corresponding to a second image of at least a portion of the subject and at least a portion of the headpiece. For example, computer-executable instructions of the second subsystem may be executed to receive second image data from an image recording device.

At block 418 of the process flow 400, it is determined, by the second subsystem and based at least in part on the first image data and the second image data, that the stimulation parameter data is associated with the subject. For example, computer-executable instructions of the second subsystem may be executed to determine, based at least in part on the first image data and the second image data, that the stimulation parameter data is associated with the subject.

At block 420 of the process flow 400, it is determined, by the second subsystem and based at least in part on the second image data, that the headpiece is associated with the subject. For example, computer-executable instructions of the second subsystem may be executed to determine, based at least in part on the second image data, that the headpiece is associated with the subject.

At block 422 of the process flow 400, it is determined, by the second subsystem and based at least in part on the second image data, that the headpiece is at a pre-determined position relative to a target anatomy of the subject. For example, computer-executable instructions of the second subsystem may be executed to determine, based at least in part on the second image data, that the headpiece is at a pre-determined position relative to a target anatomy of the subject.

At block 424 of the process flow 400, operation of a second stimulator or a second magnetic coil of the second subsystem is enabled based at least in part on the determination that the headpiece is associated with the subject. For example, computer-executable instructions of the second subsystem may be executed to enable operation of the second stimulator or the second magnetic coil based at least in part on the determination that the headpiece is associated with the subject. The second stimulator is configured to generate electric pulses. The second magnetic coil is mounted to the headpiece at a fixed location by a secure locking means and configured to deliver magnetic stimulation to the subject.

The operations described and depicted in the illustrative methods, process flows, and use cases of FIGS. 2-4 may be carried out or performed in any suitable order, such as the depicted orders, as desired in various example embodiments of the disclosure. Additionally, in certain example embodiments, at least a portion of the operations may be carried out in parallel. Furthermore, in certain example embodiments, less, more, or different operations than those depicted in FIGS. 2-4 may be performed.

Although specific embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure.

Certain aspects of the disclosure are described above with reference to block and flow diagrams of systems, methods, apparatuses, and/or computer program products according to example embodiments. It will be understood that one or more blocks of the block diagrams and flow diagrams, and combinations of blocks in the block diagrams and the flow diagrams, respectively, may be implemented by execution of computer-executable program instructions. Likewise, some blocks of the block diagrams and flow diagrams may not necessarily need to be performed in the order presented, or may not necessarily need to be performed at all, according to some embodiments. Further, additional components and/or operations beyond those depicted in blocks of the block and/or flow diagrams may be present in certain embodiments.

Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, may be implemented by special-purpose, hardware-based computer systems that perform the specified functions, elements or steps, or combinations of special-purpose hardware and computer instructions.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment. The term "based at least in part on" and "based on" are synonymous terms which may be used interchangeably herein.

What is claimed is:

1. A system for performing transcutaneous magnetic stimulation to treat a subject, the system comprising:
 a first subsystem comprising:
  at least one first memory that stores first computer-executable instructions;

at least one first processor;
a first stimulator in communication with the at least one first processor and configured to generate electric pulses;
a first magnetic coil in communication with the first stimulator and configured to deliver magnetic stimulation to a first subject; and
a first user interface in communication with the at least one first processor and configured to receive user inputs related to the magnetic stimulation delivered by the first magnetic coil to the first subject;
wherein the at least one first processor is configured to access the at least one first memory and execute the first computer-executable instructions to:
  determine first subject data associated with the first subject, the first subject data comprising one or more subject identifiers associated with the first subject;
  determine, based at least in part on one or more indications of user input from the first user interface, first stimulation parameter data comprising one or more first parameters associated with operation of the first stimulator or the first magnetic coil for the first subject; and
  cause the first subject data and the first stimulation parameter data to be stored in association with one another; and
a second subsystem in communication with the first subsystem, the second subsystem comprising:
  at least one second memory that stores second computer-executable instructions;
  at least one second processor;
  a second stimulator in communication with the at least one second processor and configured to generate electric pulses;
  a headpiece configured to engage a head of the first subject, the headpiece comprising:
    one or more headpiece identifiers associated with the headpiece; and
    a second magnetic coil in communication with the second stimulator and configured to deliver magnetic stimulation to the first subject, the second magnetic coil being mounted to a body of the headpiece at a fixed location by a secure locking means; and
  an image recording device in communication with the at least one second processor and configured to capture images of the first subject and the headpiece;
  wherein the at least one second processor is configured to access the at least one second memory and execute the second computer-executable instructions to:
    receive the first subject data and the first stimulation parameter data;
    receive first image data associated with the first subject data and the first stimulation parameter data, the first image data corresponding to one or more first images of at least a portion of the first subject and at least a portion of the headpiece;
    receive second image data from the image recording device, the second image data corresponding to one or more second images of at least a portion of the first subject and at least a portion of the headpiece;
    determine, based at least in part on the first image data and the second image data, that the first stimulation parameter data is associated with the first subject; and
    determine, based at least in part on the second image data, that the headpiece is associated with the first subject.

2. The system of claim 1, wherein the one or more first parameters comprises at least one of: (i) a magnitude and a timing sequence of electric pulses to be generated by the second stimulator, (ii) a magnitude of magnetic stimulation to be delivered by the second magnetic coil, and (iii) a position of the headpiece relative to a target anatomy of the first subject.

3. The system of claim 1, wherein the at least one second processor is further configured to access the at least one second memory and execute the second computer-executable instructions to:
  enable operation of the second stimulator or the second magnetic coil based at least in part on the determination that the headpiece is associated with the first subject.

4. The system of claim 1, wherein the second subsystem further comprises a data storage in communication with the at least one second processor, and wherein the at least one second processor is further configured to access the at least one second memory and execute the second computer-executable instructions to:
  receive the first subject data, the first stimulation parameter data, and the first image data from the data storage, the first subject data, the first stimulation parameter data, and the first image data being encrypted.

5. The system of claim 1, wherein the second subsystem further comprises a data storage in communication with the at least one second processor, and wherein the at least one second processor is further configured to access the at least one second memory and execute the second computer-executable instructions to:
  receive the first subject data, the first stimulation parameter data, and the first image data from the first subsystem or a remote server via one or more networks, the first subject data, the first stimulation parameter data, and the first image data being encrypted; and
  cause the first subject data, the first stimulation parameter data, and the first image data to be stored in association with one another at the data storage.

6. The system of claim 1, wherein the second subsystem further comprises a data storage in communication with the at least one second processor, and wherein the at least one second processor is further configured to access the at least one second memory and execute the second computer-executable instructions to:
  receive second stimulation parameter data from the first subsystem, a remote server, or a user device associated with a supervising clinician via one or more networks, the second stimulation parameter data being encrypted and comprising one or more second parameters associated with operation of the second stimulator or the second magnetic coil for the first subject;
  determine that the second stimulation parameter data supersedes at least a portion of the first stimulation parameter data; and
  cause the second stimulation parameter data to be stored in association with the first subject data and the first image data at the data storage.

7. The system of claim 1, wherein the second subsystem further comprises a data storage in communication with the at least one second processor, and wherein the at least one second processor is further configured to access the at least one second memory and execute the second computer-executable instructions to:

send stimulation history data to the first subsystem, a remote server, or a user device associated with a supervising clinician via one or more networks, the stimulation history data being encrypted and comprising one or more metrics associated with one or more stimulation sessions administered to the first subject;

receive second stimulation parameter data from the first subsystem, the remote server, or the user device via the one or more networks, the second stimulation parameter data being encrypted and comprising one or more second parameters associated with operation of the second stimulator or the second magnetic coil for the first subject;

determine that the second stimulation parameter data supersedes at least a portion of the first stimulation parameter data; and cause the second stimulation parameter data to be stored in association with the first subject data and the first image data at the data storage.

8. The system of claim 1, wherein the second subsystem further comprises an audio recording device in communication with the at least one second processor and configured to capture audio recordings of the first subject, and wherein the at least one second processor is further configured to access the at least one second memory and execute the second computer-executable instructions to:

receive first audio data, the first audio data corresponding to one or more first audio recordings of the first subject;

receive second audio data from the audio recording device, the second audio data corresponding to one or more second audio recordings of the first subject; and determine, based at least in part on the first image data, the second image data, the first audio data, and the second audio data, that the first stimulation parameter data is associated with the first subject.

9. The system of claim 1, wherein the second subsystem further comprises an audio recording device in communication with the at least one second processor and configured to capture audio recordings of the first subject, and wherein the at least one second processor is further configured to access the at least one second memory and execute the second computer-executable instructions to:

receive first audio data, the first audio data corresponding to one or more first audio recordings of the first subject;

cause the second stimulator to assume a first operational state;

receive second audio data from the audio recording device, the second audio data corresponding to one or more second audio recordings of the first subject and being indicative of a first command associated with a second operational state of the second stimulator;

determine, based at least in part on the first audio data, that the second audio data is associated with the first subject; and cause the second stimulator to assume the second operational state based at least in part on the determination that the second audio data is associated with the first subject.

10. The system of claim 9, wherein the at least one second processor is further configured to access the at least one second memory and execute the second computer-executable instructions to:

receive third audio data from the audio recording device, the third audio data corresponding to one or more third audio recordings of a second subject and being indicative of a second command associated with a third operational state of the second stimulator;

determine, based at least in part on the first audio data, that the third audio data is not associated with the first subject; and cause the second stimulator to maintain the second operational state based at least in part on the determination that the third audio data is not associated with the first subject.

11. The system of claim 1, wherein the one or more second images comprises at least a portion of the one or more headpiece identifiers, and wherein the at least one second processor is further configured to access the at least one second memory and execute the second computer-executable instructions to:

determine, based at least in part on the at least a portion of the one or more headpiece identifiers, that the headpiece is associated with the first subject.

12. The system of claim 1, wherein the one or more headpiece identifiers comprises an encrypted identifier comprising at least one of: (i) a barcode, (ii) a radio frequency identification tag, and (iii) a structural pattern.

13. The system of claim 1, wherein the one or more first parameters comprises a pre-determined position of the headpiece relative to a target anatomy of the first subject, and wherein the fixed location of the second magnetic coil corresponds to the pre-determined position of the headpiece relative to the target anatomy of the first subject.

14. The system of claim 13, wherein the at least one second processor is further configured to access the at least one second memory and execute the second computer-executable instructions to:

determine, at one or more times prior to or during a treatment session and based at least in part on the second image data, that the headpiece is at the pre-determined position relative to the target anatomy of the first subject.

15. The system of claim 14, wherein the second subsystem further comprises a first indicator in communication with the at least one second processor, and wherein the at least one second processor is further configured to access the at least one second memory and execute the second computer-executable instructions to:

cause activation of the first indicator based at least in part on the determination that the headpiece is at the pre-determined position relative to the target anatomy of the first subject.

16. The system of claim 15, wherein the second subsystem further comprises a second indicator in communication with the at least one second processor, and wherein the at least one second processor is further configured to access the at least one second memory and execute the second computer-executable instructions to:

receive third image data from the image recording device, the third image data corresponding to one or more third images of at least a portion of the first subject and at least a portion of the headpiece;

determine, based at least in part on the third image data, that the headpiece is not at the pre-determined position relative to the target anatomy of the first subject; and cause activation of the second indicator based at least in part on the determination that the headpiece is not at the pre-determined position, the second indicator being indicative of a movement of the headpiece relative to the head of the first subject toward the pre-determined position relative to the target anatomy of the first subject.

17. The system of claim 16, wherein the first indicator and the second indicator are mounted to the body of the headpiece.

18. The system of claim 1, wherein the image recording device is mounted to the body of the headpiece.

19. The system of claim 18, wherein the second subsystem further comprises a mirror configured to reflect light, and wherein the one or more second images comprises the at least a portion of the first subject and the at least a portion of the headpiece reflected by the mirror.

20. The system of claim 1, wherein the at least one second processor is further configured to access the at least one second memory and execute the second computer-executable instructions to:
receive third image data from the image recording device, the third image data corresponding to one or more third images of at least a portion of the first subject;
determine, based at least in part on the third image data, a state of the first subject, the state of the first subject comprising one of: (i) an awake state, (ii) an asleep state, and (iii) a seizure state; and
enable or disable operation of the second stimulator or the second magnetic coil based at least in part on the state of the first subject.

21. The system of claim 20, wherein the state of the first subject comprises the asleep state, wherein the second subsystem further comprises an alarm in communication with the at least one second processor, and wherein the at least one second processor is further configured to access the at least one second memory and execute the second computer-executable instructions to:
cause activation of the alarm based at least in part on the state of the first subject.

22. The system of claim 20, wherein the state of the first subject comprises the seizure state, and wherein the at least one second processor is further configured to access the at least one second memory and execute the second computer-executable instructions to:
disable operation of the second stimulator or the second magnetic coil based at least in part on the state of the first subject; and
send an emergency message to the first subsystem, a user device associated with a supervising clinician, or a user device associated with an emergency response service based at least in part on the state of the first subject, the emergency message being indicative of the seizure state.

23. The system of claim 1, wherein the second subsystem further comprises a second user interface in communication with the at least one second processor, and wherein the at least one second processor is further configured to access the at least one second memory and execute the second computer-executable instructions to:
cause the second stimulator to assume a first operational state;
receive an indication of interaction by the first subject with the second user interface, the indication of interaction being associated with a second operational state of the second stimulator; and
cause the second stimulator to assume the second operational state based at least in part on the indication of interaction.

24. The system of claim 1, wherein the second subsystem is portable and configured for use at a remote location relative to the first subsystem.

25. A method for performing transcutaneous magnetic stimulation to treat a subject, the method comprising:

determining, by at least one first processor coupled to at least one first memory of a first subsystem, first subject data associated with a first subject, the first subject data comprising one or more subject identifiers associated with the first subject;
causing, by the at least one first processor, a first stimulator of the first subsystem to generate a first plurality of electric pulses;
causing, by the at least one first processor, a first magnetic coil of the first subsystem to deliver first magnetic stimulation to the first subject;
determining, by the at least one first processor and based at least in part on one or more indications of user input from a first user interface of the first subsystem, first stimulation parameter data comprising one or more first parameters associated with operation of the first stimulator or the first magnetic coil for the first subject;
causing, by the at least one first processor, the first subject data and the first stimulation parameter data to be stored in association with one another;
receiving, by at least one second processor coupled to at least one second memory of a second subsystem, the first subject data and the first stimulation parameter data;
receiving, by the at least one second processor, first image data associated with the first subject data and the first stimulation parameter data, the first image data corresponding to one or more first images of at least a portion of the first subject and at least a portion of a headpiece, the headpiece comprising one or more headpiece identifiers associated with the headpiece;
receiving, by the at least one second processor, second image data from an image recording device of the second subsystem, the second image data corresponding to one or more second images of at least a portion of the first subject and at least a portion of the headpiece;
determining, by the at least one second processor and based at least in part on the first image data and the second image data, that the first stimulation parameter data is associated with the first subject;
determining, by the at least one second processor and based at least in part on the second image data, that the headpiece is associated with the first subject; and
enabling, by the at least one second processor and based at least in part on the determination that the headpiece is associated with the first subject, operation of a second stimulator of the second subsystem or a second magnetic coil of the headpiece, the second stimulator being configured to generate electric pulses, and the second magnetic coil being mounted to a body of the headpiece at a fixed location by a secure locking means and configured to deliver magnetic stimulation to the first subject.

26. The method of claim 25, further comprising:
sending, by the at least one second processor, stimulation history data to the first subsystem, a remote server, or a user device associated with a supervising clinician via one or more networks, the stimulation history data being encrypted and comprising one or more metrics associated with one or more stimulation sessions administered to the first subject;
receiving, by the at least one second processor, second stimulation parameter data from the first subsystem, the remote server, or the user device via the one or more networks, the second stimulation parameter data being encrypted and comprising one or more second parameters associated with operation of the second stimulator or the second magnetic coil for the first subject;

determining that the second stimulation parameter data supersedes at least a portion of the first stimulation parameter data; and causing the second stimulation parameter data to be stored in association with the first subject data and the first image data at a data storage of the second subsystem.

27. The method of claim 25, further comprising:

causing, by the at least one second processor, the second stimulator to assume a first operational state;

receiving, by the at least one second processor, an indication of interaction by the first subject with a second user interface of the second subsystem, the indication of interaction being associated with a second operational state of the second stimulator; and causing, by the at least one second processor and based at least in part on the indication of interaction, the second stimulator to assume the second operational state.

* * * * *